(12) United States Patent
Jaber

(10) Patent No.: US 12,042,644 B2
(45) Date of Patent: Jul. 23, 2024

(54) ADJUSTABLE LENGTH NEEDLE HOUSING

(71) Applicant: Jaber Medical, PLLC, Houston, TX (US)

(72) Inventor: Noor Mahmoud Jaber, Houston, TX (US)

(73) Assignee: Jaber Medical, PLLC, Houston, TX (US)

( * ) Notice: Subject to any disclaimer, the term of this patent is extended or adjusted under 35 U.S.C. 154(b) by 844 days.

(21) Appl. No.: 17/052,743

(22) PCT Filed: May 6, 2019

(86) PCT No.: PCT/US2019/000023
§ 371 (c)(1),
(2) Date: Nov. 3, 2020

(87) PCT Pub. No.: WO2019/212604
PCT Pub. Date: Nov. 7, 2019

(65) Prior Publication Data
US 2021/0228817 A1    Jul. 29, 2021

Related U.S. Application Data

(60) Provisional application No. 62/817,895, filed on Mar. 13, 2019, provisional application No. 62/666,830, filed on May 4, 2018.

(51) Int. Cl.
A61M 5/32     (2006.01)
A61M 5/46     (2006.01)

(52) U.S. Cl.
CPC ........ A61M 5/3213 (2013.01); A61M 5/3216 (2013.01); A61M 5/46 (2013.01)

(58) Field of Classification Search
CPC .... A61M 5/3213; A61M 5/3216; A61M 5/46; A61M 2005/3217; A61M 2005/3247; A61M 5/3257
See application file for complete search history.

(56) References Cited

U.S. PATENT DOCUMENTS 6,015,397 A  *  1/2000  Elson .................. A61M 5/3275
                                                        604/263
7,141,286 B1    11/2006  Kessler et al.
(Continued)

OTHER PUBLICATIONS

Int'l Search Report and Written Opinion received in copending PCT Application No. PCT/US2019/000023 dated Sep. 4, 2019, 4 pages.

Primary Examiner — Robert J Utama
Assistant Examiner — Hamza A Darb
(74) Attorney, Agent, or Firm — Womble Bond Dickinson (US) LLP

(57) ABSTRACT

Exposed lengths of needles of needle assemblies are adjusted with a needle housing. Also, a cap assembly for use with a needle system selectively covers a tip portion of the needle system. The cap assembly includes a body made up of segments, where one or more of the segments retractably exposes a designated length of the tip portion. When exposed, the tip portion is insertable into a subject object or organism to a depth substantially that of the designated length. In one embodiment the segments are hingedly affixed to one another, and retraction involves pivoting one or more of the segments. In another embodiment, the body is shortened by axially moving a segment with respect to another segment. In an example, the needle system includes a needle assembly having a shaft, a lumen in the shaft, and a bevel on a free end of the shaft.

16 Claims, 26 Drawing Sheets

(56) References Cited

U.S. PATENT DOCUMENTS

| | | |
|---|---|---|
| 2011/0125056 A1 | 5/2011 | Merchant |
| 2015/0090625 A1 | 4/2015 | Bauss |
| 2015/0094659 A1* | 4/2015 | Schraga .............. A61M 5/3205 604/110 |
| 2016/0317755 A1* | 11/2016 | Wang .................. A61M 5/3216 |
| 2017/0281878 A1* | 10/2017 | Wickham .............. A61M 5/326 |

* cited by examiner

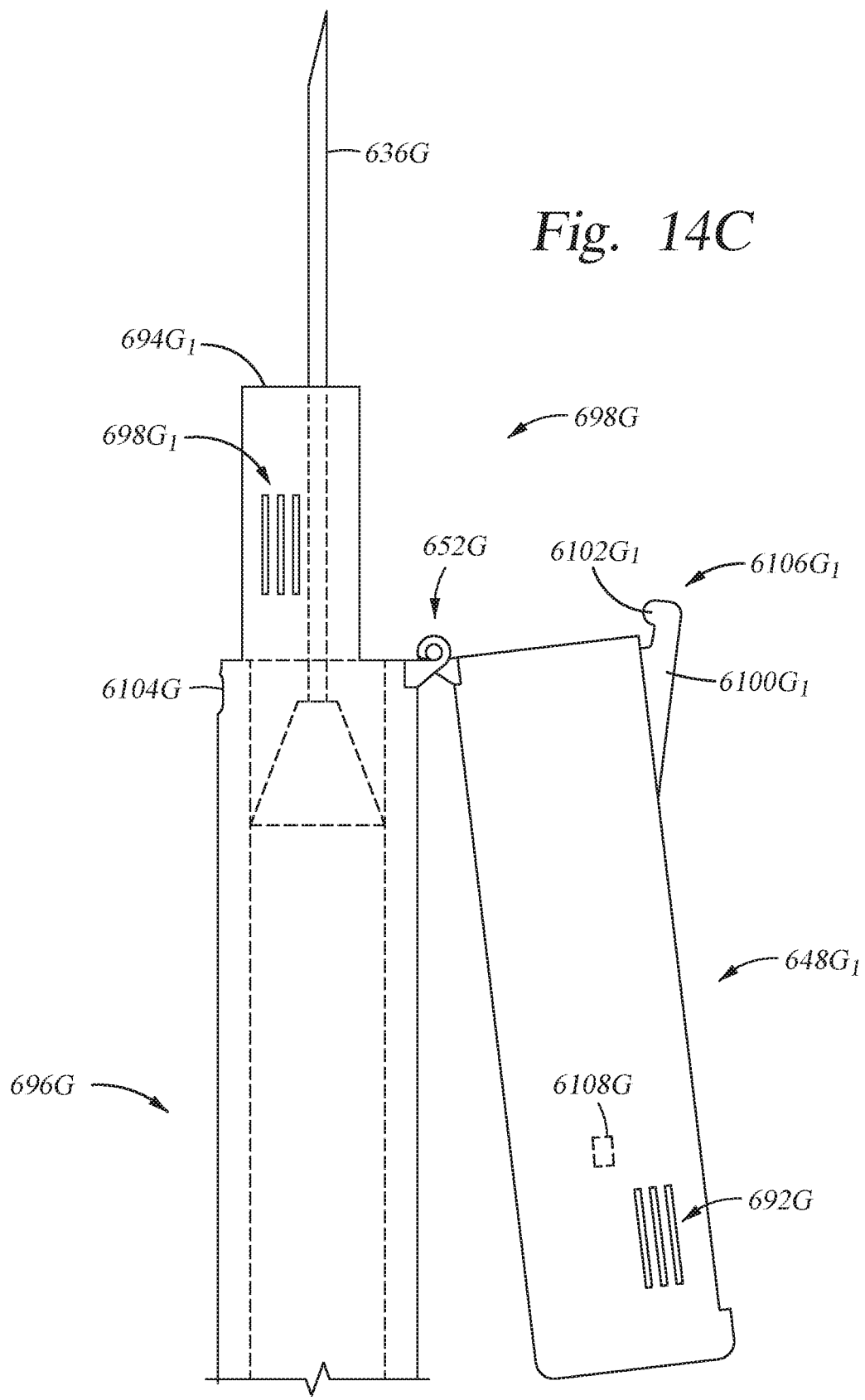

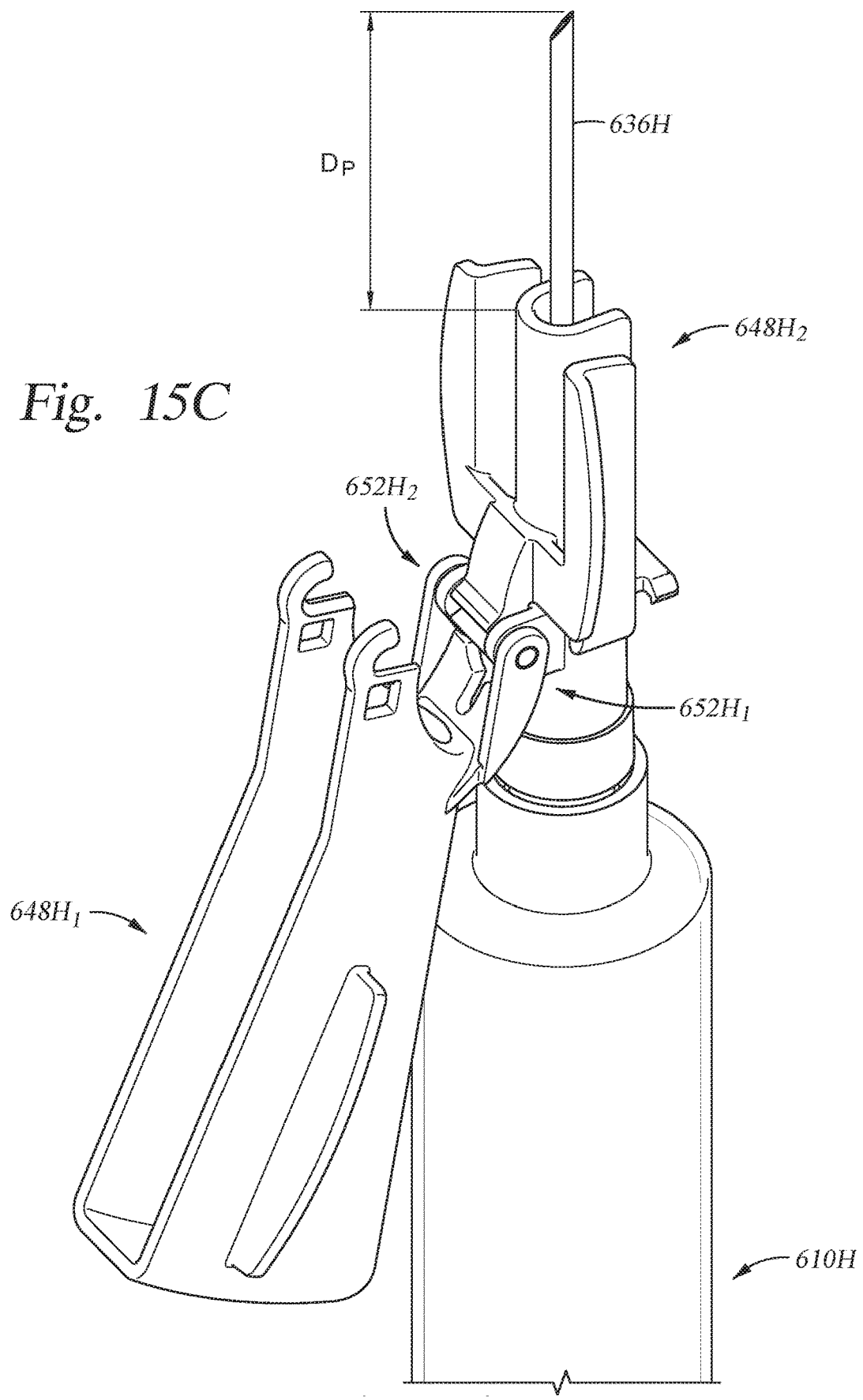

ADJUSTABLE LENGTH NEEDLE HOUSING

CROSS REFERENCE TO RELATED APPLICATIONS

This application is a U.S. National Phase Under 35 U.S.C. § 371 of International Application No. PCT/US2019/000023, filed May 6, 2019, titled "Adjustable Length Needle Housing," which claims priority to, and the benefit of, U.S. Provisional Application No. 62/666,830, filed May 4, 2018, titled "Adjustable Length Needle Housing," and U.S. Provisional Application No. 62/817,895, filed Mar. 13, 2019, titled "Retractable Needle Guard," each of which is incorporated herein by reference in its entirety.

TECHNICAL FIELD

The present disclosure relates to assemblies that are in invasive communication with organisms, such animals and humans; and where the assemblies include a tip portion that penetrates the organisms. More specifically, the present disclosure relates to needle assemblies for use in delivering or extracting materials to and from animals and humans.

BACKGROUND

Needles are generally one size fits all. In many instances, the needle is too long to be completely inserted under the skin/injected. This is especially true when administering injections or doing procedures, such as deploying a catheter system. It is also difficult to control the insertion depth of the needle. And, this can cause iatrogenic injuries/needle breaks. Currently, the needle guards in the market do not address these issues and these are designed to prevent accidental needlestick injuries after use on a patient.

SUMMARY

Disclosed herein are apparatuses and methods addressing the shortcomings of the art, and may provide any number of additional or alternative advantages. The present disclosure relates to assemblies in communication with organisms via a needle and having a guard over the needle that is selectively retractable to expose the needle to selective lengths.

This needle housing is also configured to act as a needle guard and prevent the needle from being inserted any deeper than is desired/required. Certain embodiments include a needle housing with a body having (i) an exterior wall with one or more circumferential perforations perpendicular to longitudinal axis of the body and defining an inner cavity to house a needle; and (ii) a mouth configured to receive the needle. Certain embodiments include a needle housing with a body having (i) a first segment with a mouth configured to receive a needle and secure the needle housing to a hub of the needle; (ii) a second segment that is detachable from the first segment and moves coaxially on the needle; and (iii) a locking fixture in contact with the first segment and the second segment and configured to secure the distance between the first segment and the second segment on the needle, when in locked position.

Another embodiment is a needle assembly that contains a needle and a needle housing. The needle housing has an exterior wall defining an inner cavity to house the needle and a mouth configured to receive the needle and secure the needle housing to a hub of the needle. This housing can be separated into two or more segments by exerting force on a perforation on the body perpendicular to longitudinal axis of the body. In certain embodiments, the two or more segments of the needle housing are of equal length. In certain embodiments, the two or more segments of the needle housing are of unequal length. The needle housing can be made of a synthetic polymer material. In certain embodiments, the needle housing can be made of one or more of plastic, silicone, rubber, or resin. In certain embodiments, at least two segments of the needle housing can be connected by a glide guard.

The needle system described here can be used with a syringe or a catheter to deliver a composition to an organism or withdraw a bodily fluid from an organism. Disclosed is an example of a cap assembly for use with a needle system, and which includes a base segment that selectively mounts to the needle system, and a first segment coupled with the base segment. The first segment is moveable between a deployed configuration that covers a tip portion of the needle system, and a retracted configuration that exposes a designated distance of the tip portion. In an example, the tip portion includes an elongated shaft, a lumen formed axially through the shaft, and a bevel on a free end of the shaft. In one alternative, the first segment and base segment make up a body having a cavity that receives the shaft, and that when in the deployed configuration provide a barrier between contact of the bevel with another object. The first segment alternatively pivots about an axis of the base segment when moved between the retracted and deployed configurations. The assembly optionally further includes an elongated slot formed axially through a sidewall of the first segment, so that when the first segment pivots between the retracted and deployed configurations the tip portion passes through the slot. An example of a clasp assembly is optionally included having elements that are attached to the first segment and the base segment, so that when the first and base segments are in the deployed configuration, a clasp force is transferred across the elements and between the first segment and the second segment. Embodiments exist having a hinge assembly coupled to the first segment and about which the first segment pivots. The assembly optionally includes a second segment coupled to the first segment and coupled to the base segment, where the second segment is pivotal with respect to the first segment and the base segment. In this example, the first segment pivots about an axis that is transverse to an axis about which the second segment pivots. Embodiments exist where the first segment and base segment are substantially coaxial, and where the first segment moves axially with respect to the base segment when moved between the retracted and deployed configurations. A tab is optionally formed on an inner surface of the first segment, and a groove that extends axially along an outer surface of the base segment, so that when the tab is aligned with the groove, the first segment is axially moveable along a length of the base segment. Embodiments exist having step members arranged axially along the base segment, and wherein the groove is formed between ends of the step members. The tab is optionally insertable between adjacent step members. In an example, threads are formed on an inner surface of the first segment, and threads on an outer surface of the base segment, so that the first segment is moved axially with respect to the base segment with rotation between the first segment and base segments. Further optionally included is an aperture axially formed through an end of the first segment distal from the base segment, and which receives the tip portion.

Also described herein is a method of using a needle system, and which includes receiving a cap assembly that covers a tip portion of the needle system, retracting a portion of the cap assembly to expose a designated distance of the tip portion, and blocking contact between the tip portion and another object by moving the portion. An optional further step includes inserting the tip portion into a subject up to the designated distance when the tip portion is exposed. In an alternative, retracting involves pivoting the portion of the cap assembly with respect to a remaining portion of the cap assembly. In another alternative, retracting involves moving the portion of the cap assembly axially with respect to a remaining portion of the cap assembly. Examples of the tip portion include a shaft with a bevel on a free end.

Numerous other aspects, features and benefits of the present disclosure may be made apparent from the following detailed description taken together with the drawing figures. The needle assemblies can include other components depending on desired treatment goals. It should be further understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure.

FIG. 14C is a side view of the embodiment of the guard assembly of FIGS. 14A and 14B in a retracted configuration.

FIGS. 15A-15E are views of alternate embodiments of the guard assembly of FIGS. 14A-14E.

DETAILED DESCRIPTION

Figures 1, 2:
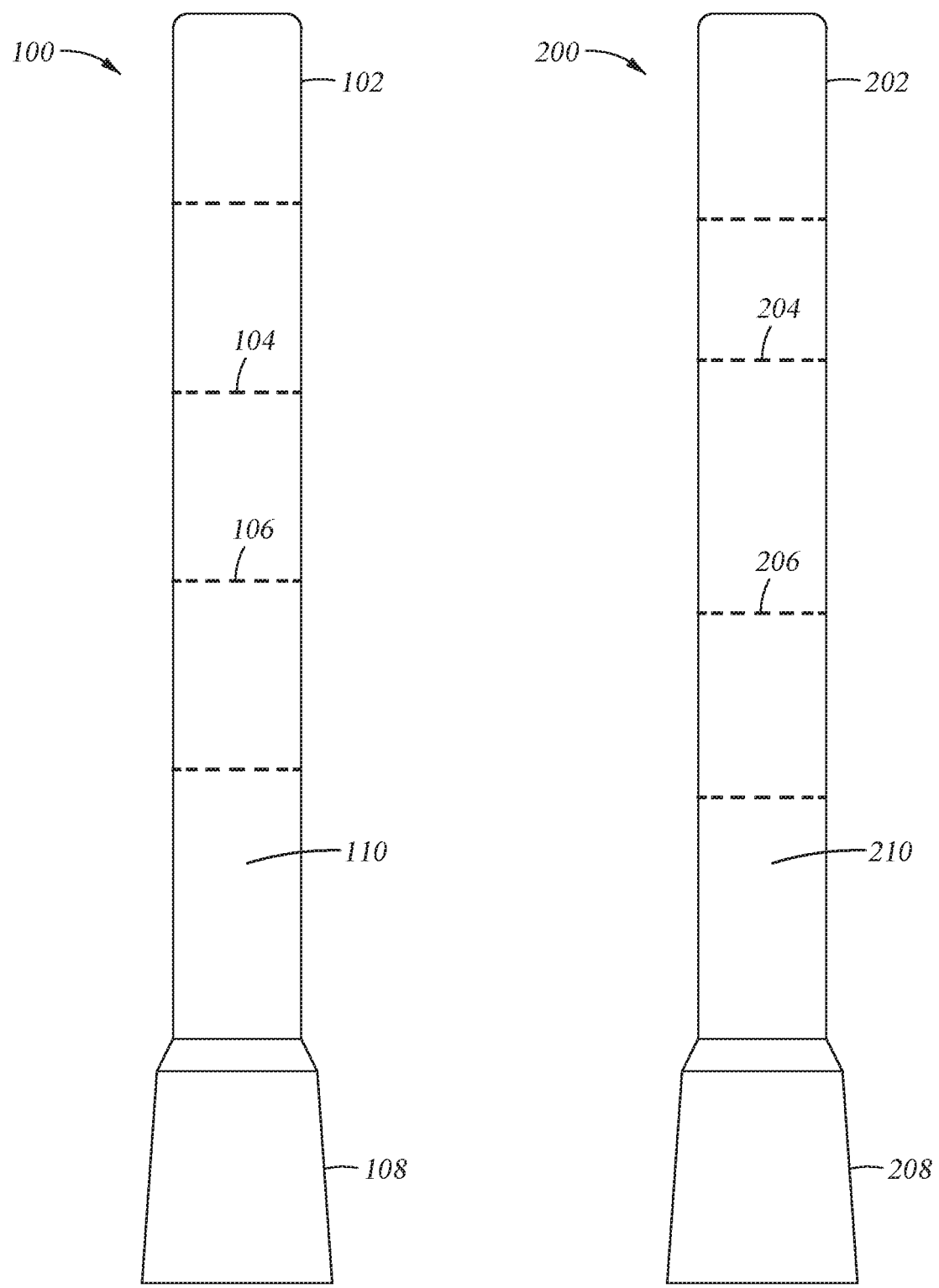
FIG. 1 is a diagrammatic representation of an embodiment of a needle housing.
FIG. 2 is a diagrammatic representation of another embodiment of a needle housing.

Disclosed here are various embodiments of a needle housing and methods of use of the needle housing to deliver or extract fluids or solids from an animal. In certain embodiments, the needle housing has an inner cavity to house a needle and an end to secure the housing to the needle. The needle housing has one or more perforations configured to split the housing into two or more segments. Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

The term "housing" as used here refers to a rigid sheath that partially or completely encloses a needle. The term "perforation" as used here refers to a line of weakness on the body of the housing configured to assist with separation of the housing into two or more detachable segments.

Embodiments disclosed here enable an individual to detach a portion of the needle housing and reuse the remaining portion of the needle housing as a guard. This housing helps prevent iatrogenic injuries and needle breaks. This housing also improves patient satisfaction when having injections/aspirations performed. In certain embodiments, the housing is a part of a needle that is manually attached to a conventional syringe. In other embodiments, the housing is part of a needle that is coupled to a commercially prepared pre-filled syringe.

Embodiments of the needle housing are made with plastic using injection molding. The mold is designed to create a needle housing with two or more circumferential perforations at predetermined locations. These perforations would allow for easy removal of one or more segments of the needle housing. The needle housing can be removably or irremovably secured to a needle, a needle assembly or a syringe. In certain embodiments, the housing is removably secured to the hub of the needle. In an embodiment, the needle housing fits over around the hub of the needle. In another embodiment, the needle housing can snap onto or around the hub of a needle attached to a syringe. After the needle housing is mounted on the needle, one or more segments of the needle housing can be removed to expose the needle at the required length for use with the patient.

Various embodiments of the needle housing can utilize different types of mechanisms to detach the segments. The segments can be completely or partially detached simply by hand. In an embodiment, in order to remove a segment, a slight twist can be imparted to the housing at the appropriate perforation, such that the segments of the housing proximate to the base of the needle remain fixed but the segments of the housing proximate to the tip of the needle rotate and are detached from the housing. In another embodiment, a projection can be provided as part of each segment of the housing, such that movement of the projection around the circumferential perforation detaches the segments. For example, the projections can be a tab or a hinge coupled to the perforations on the body of the housing and an individual takes hold of the tab or hinge and rotates around the perforation to detach the required segment of the needle housing. In other embodiments, the segments can be designed such that they are completely or partially detached by use of an external cutting instrument, such as a knife or a pair of scissors. For example, an individual may employ an external cutting device such as a knife or a pair of scissors for cutting along the circumferential perforation to detach the segments The needle housing can be manufactured with different external and internal body shapes. In an embodiment, the body can have a cylindrical external shape with a cylindrical inner cavity enclosing the needle in a coaxial configuration. In an embodiment, the body can have a cylindrical external shape with a cylindrical inner cavity enclosing the needle in an eccentric configuration, where the inner cavity is offset within the body of the housing. In another embodiment, the body can have a cuboidal external shape with a cylindrical inner cavity enclosing the needle in a coaxial or an eccentric configuration. The external and internal body shapes can be a blend of two or more shapes. The inner cavity can be centrally located within the body of the housing or can be offset within the body of the housing. The housing can be removably or irremovably secured to the needle hub.

In an embodiment, the needle may be of hollow construction, example for, for use as drawing blood or delivering a drug. In an embodiment, the needle may be of solid construction, example for, for use as a suture needle. Various embodiments of the needle housing can accommodate various lengths and various gauges of the needles. Hospitals tend to stock needle assemblies with needles of the same gauge but multiple different lengths. Using the various embodiments disclosed here permits an individual to stock needle assemblies with needles of the same gauge and length, as he can tailor the length of the exposed needle to the requirements of the procedure being performed. This would simplify the inventory and the production process, For example, during immunization drives, a family doctor or a veterinarian can carry several needle assemblies with needles of the same gauge and length, and tailor the length of the exposed needle depending on the patients who turn up for the drive. In another example, a healthcare professional can tailor the required length of the exposed needle depending on the depths at which fluids need to be aspirated during a procedure. In another example, a healthcare professional can tailor the length of the exposed needle depending on visualization of the location of the vital organs of a particular patient.

In certain embodiments, the needle housing has a glide guard that engages two segments of the needle housing and secures these segments once the appropriate length of the shaft is exposed. In an embodiment, the glide guard has two members—a fixed member and a moveable member, and a locking mechanism. The fixed member of the glide guard is irremovably secured to that last segment of the needle housing proximate to the base of the needle. The moveable member of the glide guard is irremovably secured to the penultimate segment of the needle housing proximate to the base of the needle. The penultimate segment of the needle housing can move coaxially along the length of the needle shaft to the maximum distance permitted by the moveable member of the glide guard. When the appropriate length of the needle shaft is exposed beyond the penultimate segment of the needle housing, the glide guard is placed in the locked position by using the locking mechanism. In the locked position, the penultimate segment of the needle housing is held immobile. In an embodiment, the locking mechanism locks the movement of the moveable member of the glide guard by engaging a gripping surface of the moveable member of the glide guard on the shaft of the needle. In another embodiment, the locking mechanism can be part of the moveable member of the glide guard. For example, the moveable member of the glide guard can engage the penultimate segment of the needle housing such that a screwing mechanism renders the penultimate segment of the needle housing immobile at a particular location on the shaft of the needle.

In another embodiment, the needle housing contains a first segment defining a first coaxial inner cavity through which a needle can pass and having with a mouth configured to receive the needle and secure the needle housing to a hub of the needle; a second segment defining a second coaxial inner cavity through which the needle can pass and configured to move coaxially on the needle; and a locking fixture in contact with the first segment and the second segment. The locking fixture in an open position permits coaxial movement of the second segment away from the first segment of the needle housing. The locking fixture, when in locked position, secures the second segment on the needle at a determined distance away from the first segment and prevents further movement of the second segment.

FIG. 1 is a diagrammatic representation of a needle housing, according to an exemplary embodiment. Referring to FIG. 1, the needle housing 100 has segments separated in regular intervals by perforations. The needle housing 100 includes a body 102, perforations 104 and 106, and an end 108 configured to receive a needle. The inner cavity 110 of the body 102 is disposed concentrically. All perforations, including 104 and 106, are placed at regular intervals. Detachment of the housing at perforation 104 will result in less of the needle being exposed as compared to separation of the housing at perforation 106.

FIG. 2 is a diagrammatic representation of a needle housing, according to an exemplary embodiment. Referring to FIG. 2, the needle housing 200 has segments separated at different length intervals by perforations. The needle housing 200 includes a body 202, perforations 204 and 206, and an end 208 configured to receive a needle. The inner cavity 210 of the body 202 is disposed concentrically. All perforations, including 204 and 206, are provided such that detachment of the housing at the perforations results in segments of different lengths. Detachment of the housing at perforation 104 will result in a greater portion of the needle being exposed as compared to the portion exposed by detachment of the housing at perforation 204.

Figures 3A, 3B:
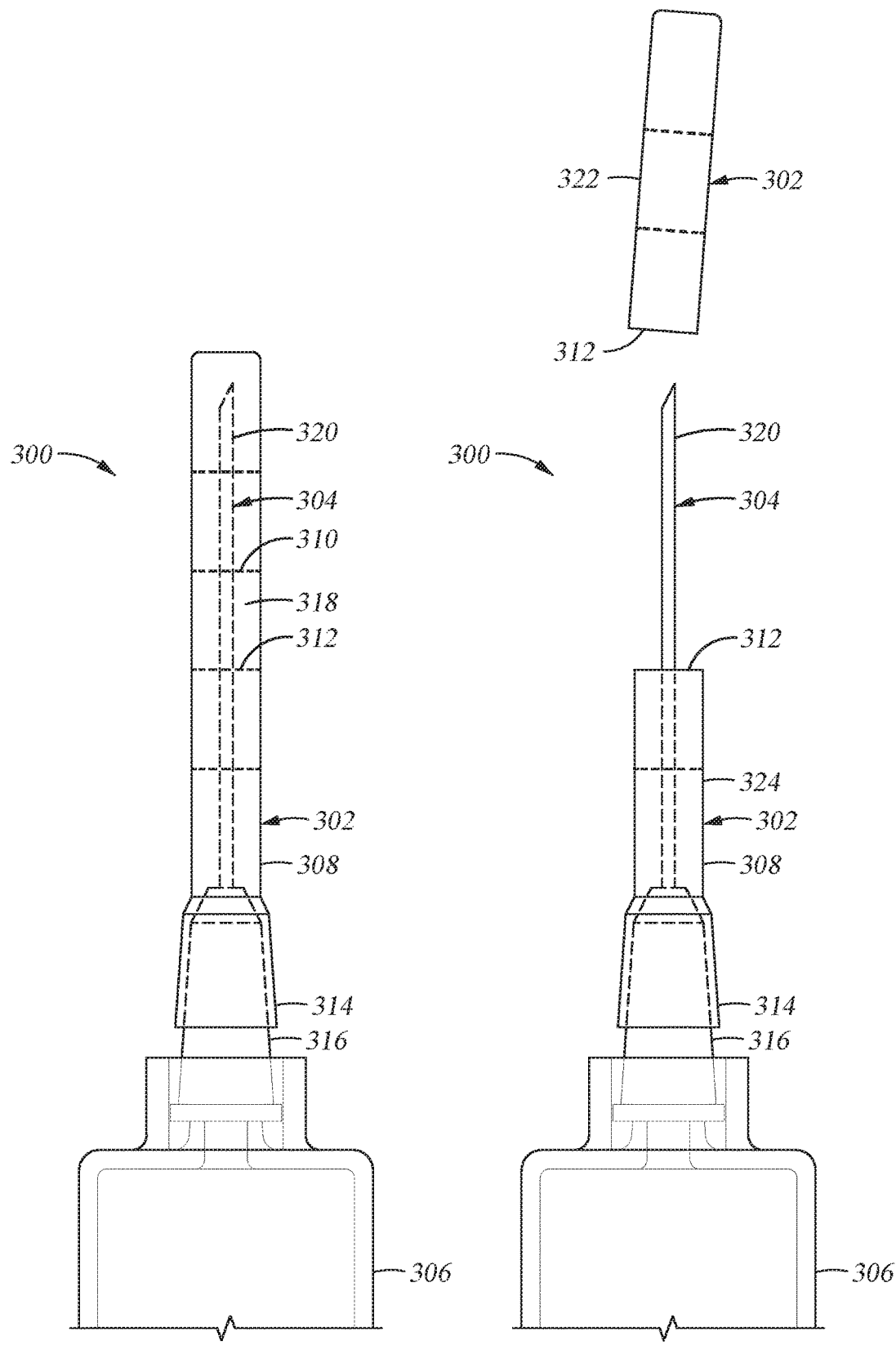
FIGS. 3A and 3B are diagrammatic representations of a needle assembly before and after a segment of the needle housing is removed.

FIGS. 3A and 3B are diagrammatic representations of a needle assembly before and after a segment of the needle housing is removed, according to an exemplary embodiment. Referring to FIG. 3A, the needle assembly 300 has a needle housing 302 and a needle 304 attached to a syringe 306. The needle housing 302 has segments separated in regular intervals by perforations. The needle housing 302 includes a body 308, perforations 310 and 312, and an end 314 configured to fit around the hub 316 of the needle 304. The inner cavity 318 of the body 308 is disposed concentrically to enclose the shaft 320 of the needle 304.

Referring to an embodiment described in FIG. 3B, the needle assembly 300 has a needle 304 attached to a syringe 306. In order to remove a segment, a slight twist or tear can be imparted to the housing 302 at the perforation 312. The needle housing 302 of FIG. 3A has been separated into two separate pieces, 322 and 324 by utilizing the perforation 312. The piece of the housing proximate to the base of the needle 324 remains fixed around the hub 316 of the needle 304 via the end 314. The needle housing piece 322 functions as a guard to dictate the exposed length of the shaft 320 of the needle 304. The segments of the housing proximate to the tip of the needle have been detached from the housing 302. The detached needle housing piece 324 is appropriately disposed.

Figures 4A, 4B:
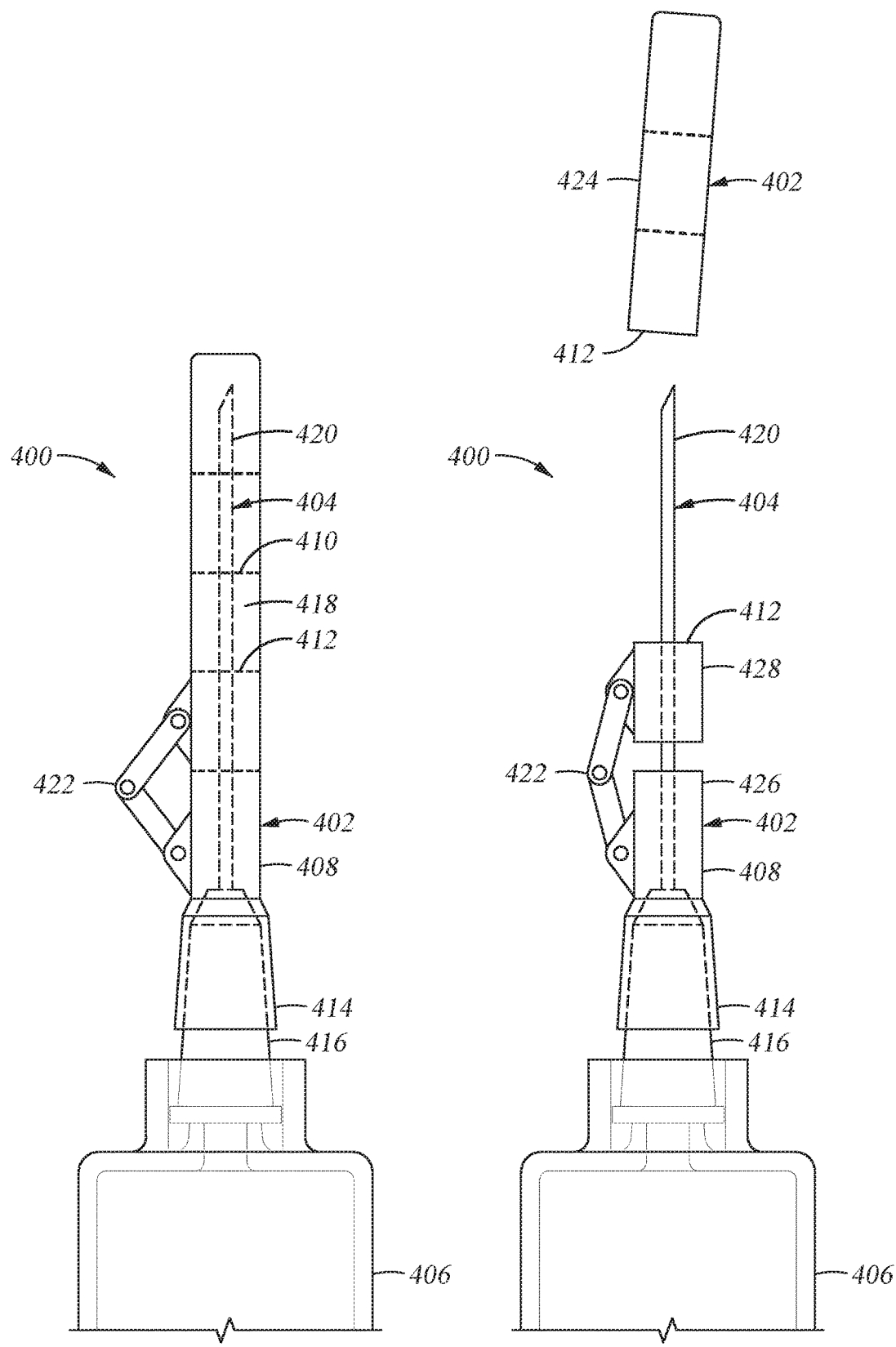
FIGS. 4A and 4B are diagrammatic representations of a needle assembly with a glide guard, before and after a segment of the needle housing is removed.

FIGS. 4A and 4B are diagrammatic representations of a needle assembly with a glide guard, before and after a segment of the needle housing is removed, according to another exemplary embodiment.

Referring to an embodiment described in FIG. 4A, the needle assembly 400 has a needle housing 402 and a needle 404 attached to a syringe 406. The needle housing 402 has segments separated in regular intervals by perforations. The needle housing 402 includes a body 408, perforations 410 and 412, and an end 414 configured to fit around the hub 416 of the needle 404. The inner cavity 418 of the body 408 is disposed concentrically to enclose the shaft 420 of the needle 404. A glide guard 422 is provided connecting two segments proximate to the hub 416.

Referring to an embodiment described in FIG. 4B, the needle assembly 400 has a needle 404 attached to a syringe 406. In order to remove a segment, a cut is imparted to the housing 402 at the perforations 410 and 412. The piece of the housing proximate to the base of the needle 426 remains fixed around the hub 416 of the needle 404 via the end 414. The penultimate segment 428 of the housing is released to move linearly around the shaft of the needle but guided by the glide guard 422. The glide guard 422 has a locking mechanism whereby once the appropriate length of the shaft 420 has been exposed, the locking mechanism is engaged to prevent further movement of penultimate segment 428. The penultimate segment 428 functions as a guard to dictate the exposed length of the shaft 420 of the needle 404. The segments of the housing proximate to the tip of the needle have been detached from the housing 402. The detached needle housing piece 424 is appropriately disposed. Embodiments exist where one end of the glide guard 422 connects to a segment, and the other end attaches to or mounts directly to syringe 406.

Figure 5:
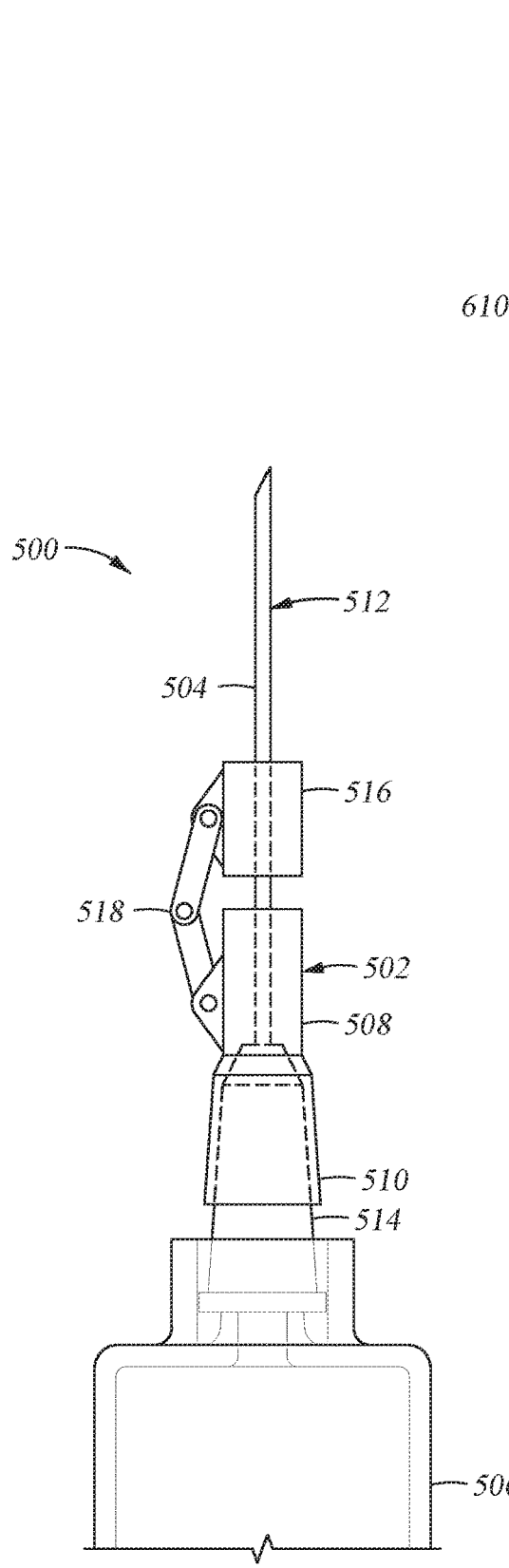
FIG. 5 is a diagrammatic representation of a needle assembly with two segments and a locking fixture.

Referring to an embodiment described in FIG. 5, the needle assembly 500 has a needle housing 502 and a needle 504 attached to a syringe 506. The needle housing 502 contains a first segment 508 defining a coaxial inner cavity through which a needle can pass and a mouth 510 configured to receive a needle 512 and secure the first segment 508 to a hub 514 of the needle 512. The needle housing 502 contains a second segment 516 configured to move coaxially on the needle 512. The needle housing 502 further contains a locking fixture 518 in contact with the first segment 508 and the second segment 516. The locking fixture 518 in an open position permits coaxial movement of the second segment 516 away from the first segment 508 of the needle housing 502. The locking fixture 518, when in locked position, secures the second segment 516 on the needle 512 at a determined distance away from the first segment 508 and prevents further movement of the second segment 516.

Figure 6:
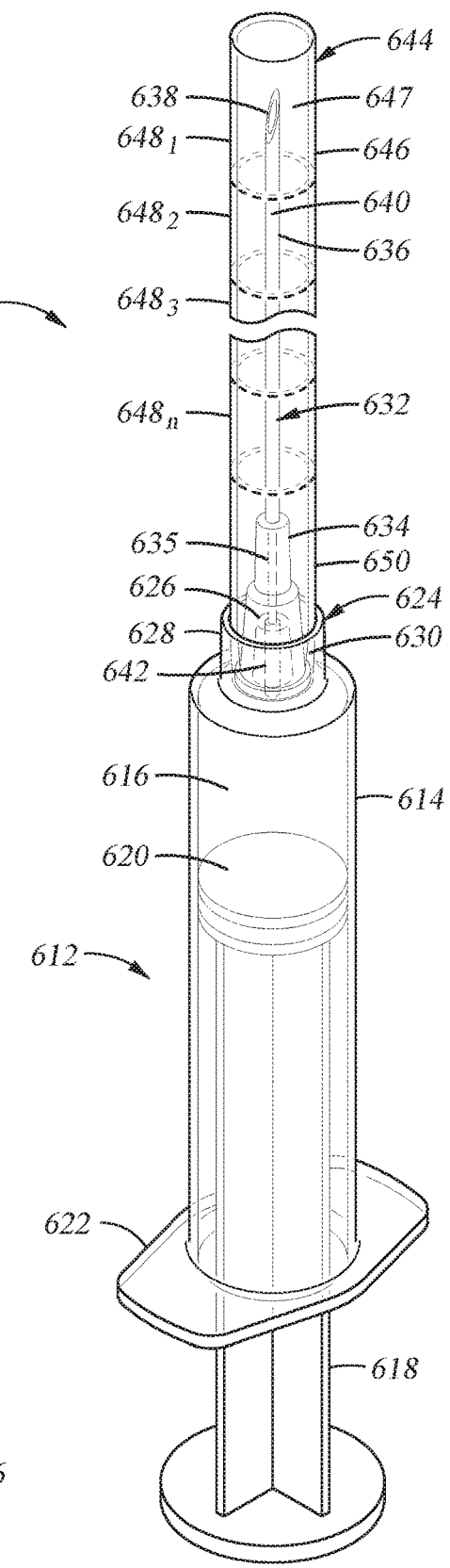
FIG. 6 is a perspective view of an example of a system for invasive communication having a syringe, needle, and guard assembly.

Shown in perspective view in FIG. 6 is one example of a needle assembly 610, which in this example is used for injecting or drawing fluids to or from a subject. Examples of the subject include organisms such as an animal or human, as well as inanimate objects. Included with assembly 610 is a syringe 612 that includes a barrel 614. As shown barrel 614 is substantially cylindrical, and a chamber 616 is defined within barrel 614. In an example, fluid (not shown) is housed in chamber 616, which is injected into or drawn from the subject. A plunger 618 is included in this example, which is an elongated cylindrical member having a plunger head 620 that inserts into chamber 616. Steps of injecting or withdrawing are accomplished by reciprocating piston head 620 within chamber 616 in a designated direction. A planar flange 622 is shown mounted around an opening of chamber 616, and to which a counter-force is selectively applied when reciprocating plunger 618.

Further in the example of FIG. 6, a fitting 624 mounts to an end of syringe 612 distal from flange 622; and which includes a cylindrically shaped tip 626 and an annular collar 628 that circumscribes tip 626. Tip 626 is depicted in the FIG. 6 as being generally concentric within collar 24; an annulus 630 is defined in the space between tip 626 and collar 628. Fitting 624 provides an attachment point for a needle assembly 632. In the illustrated embodiment, needle assembly 632 includes a frusto-conically shaped hub 634 that includes a port 635 extending axially therethrough. A larger diameter end of hub 634 inserts into the fitting 624; an outer periphery of hub 634 is shown circumscribed within an inner surface of collar 628 and the tip 626 inserts into port 635. An elongated shaft 636 projects axially from the smaller diameter end of hub 634; a bevel 638 is shown provided on a free end of shaft 636 that defines a sharp end suitable for penetrating through the outer surface of a subject. A lumen 640 extends axially within shaft 636 and defines a passageway for fluid communication from bevel 638 to, hub 634, tip 626, and into chamber 616. Fluid communicates through the tip 626 via a passage 642 formed axially within tip 626.

A guard assembly 644 is included with the example of the needle system 10 of FIG. 6. Guard assembly 644 includes a solid body 646 that circumscribes the needle assembly 632 when in place. A cavity 647 is formed within body 646 which receives needle assembly 632. Body 646 forms a prophylactic barrier around needle assembly 632 to prevent bevel 638 from contacting objects not designated or intended for needle penetration. In the example of FIG. 6, body 646 is partitioned into a number of segments $648_{1-n}$, which as will be described in more detail below, are selectively retracted to expose the needle assembly 632 for penetration into a subject. Body 646 further includes a base segment 650 which defines a section of body 646 that interfaces with the fitting 624.

Figure 7A:
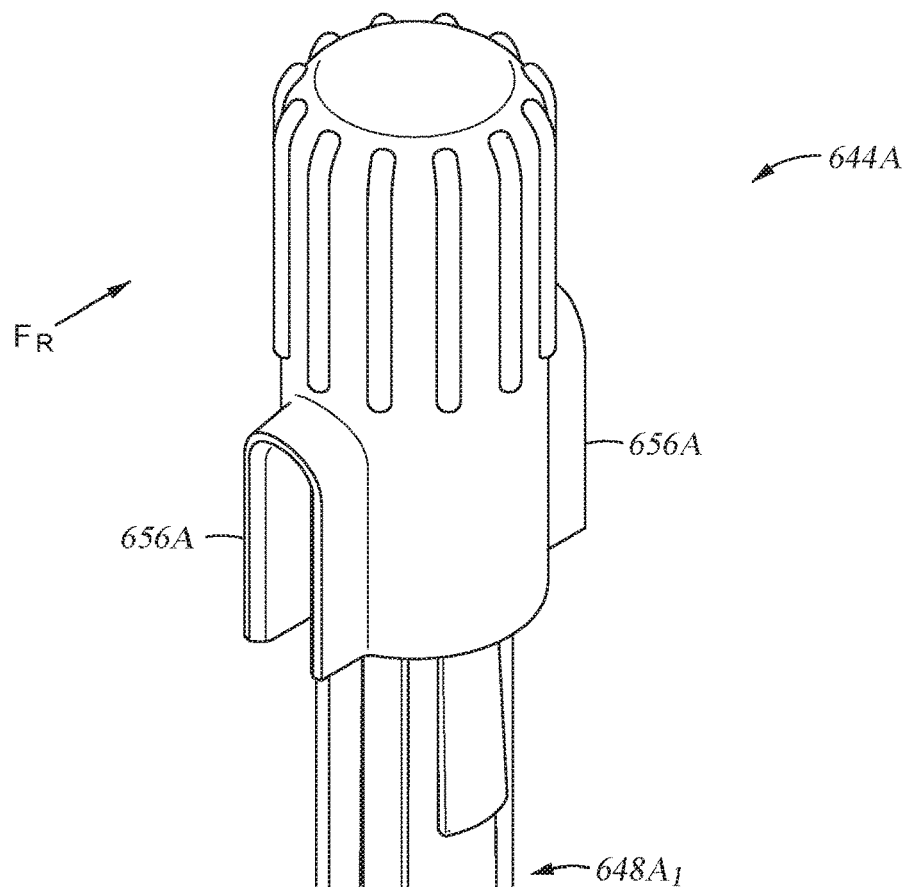
FIGS. 7A and 7B are perspective views of an embodiment of the single-length guard assembly of FIG. 6 in neutral and retracted configurations respectively.
Figure 7A:
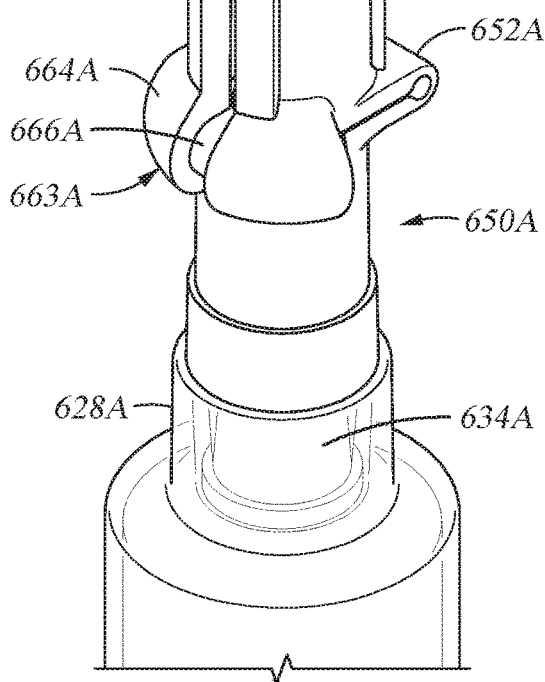
Figure 7B:
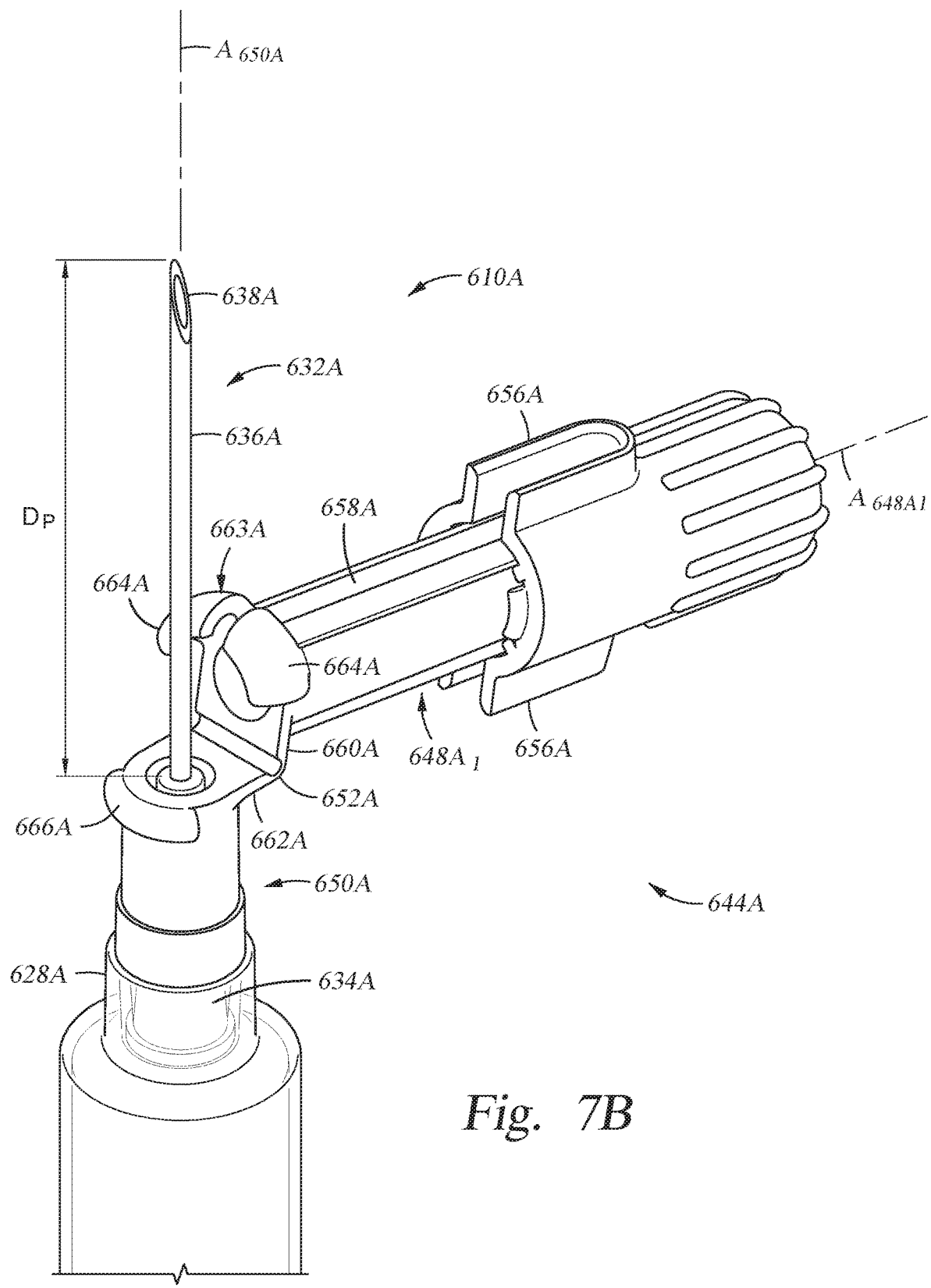

Illustrated in FIG. 7A is an example of a guard assembly 644A in a deployed configuration, and an example of guard assembly 644A in a retracted mode is shown in FIG. 7B. In the example depicted, first and second segments $648A_1$, 650A are generally elongate members. A hinge assembly 652A is provided which couples to both the first segment $648A_1$ and base segment 650A, and which enables pivoting movement of segments $648A_1$, 650A with one another. Further illustrated in FIG. 7B is that when in the retracted mode or configuration with shaft 636A and bevel 638A exposed, first segment $648A_1$ is aligned with axis $A_{648A1}$, and which is transverse to axis $A_{650A}$ in the figure, but can pivot farther such that first segment $648A_1$ is parallel to $A_{650A}$. Retracting or pivoting the segment $648A_1$ as shown in FIG. 7B exposes a portion of shaft 636A past the base segment 650A, which for the purposes of discussion herein is referred to as a designated penetration distance $D_P$. Optional tabs 656A are shown projecting radially outward from the outer surface of the first segment $648A_1$ and distal from base segment 650A. An example of a slot 658A is depicted in FIG. 7B and shown formed axially through a sidewall of a portion of the first segment $648A_1$, so that when in the retracted mode, shaft 636A passes unimpeded past the first segment $648A_1$.

The example of the hinge assembly 652A of FIG. 7B includes leaves 660A, 662A that couple respectfully with the base segment 650A and first segment $648A_1$, and which are joined to one another by an elastic and flexible connection; embodiments exist where connection is a living hinge, and alternatively include anything coupling segments 650A, $648A_1$ and allows for their respective pivoting. In this example, when guard assembly 644A is in the retracted mode of FIG. 7B, base segment 650A and first segment $648A_1$ remain attached to one another via the hinge assembly 652A. In an example of use, a subject is penetrated with the needle assembly 610A when the guard assembly 644A is in a retracted mode. Although the first segment $648A_1$ is retracted, the base segment 650A remains in place around the shaft 636A so that the entire length of shaft 636A is not exposed; which limits how deep into a subject the shaft 636A can penetrate. Thus the maximum penetration depth of the shaft 636A into a subject is set by the designated penetration distance $D_P$. Strategic positioning of the hinge assembly 652A at a particular location thus establishes the designated penetration distance $D_P$, and also establishes the maximum penetration depth of shaft 636A into the subject. An advantage disclosed herein is that a guard assembly is formable so that a penetration depth $D_P$ matches a particular application or a particular subject. It is within the capabilities of those skilled in the art to establish a penetration depth of a shaft into a particular application or subject.

Still referring to FIGS. 7A and 7B, shown is an example of a clasp assembly 663A, which maintains the generally coaxial orientation of the first segment $648A_1$ with base segment 650A when in the deployed configuration of FIG. 7A. In an example, the clasp assembly 663A is decoupled by applying a force FR, which pivots first segment $648A_1$ about base segment 650A to put first segment $648A_1$ into the retracted configuration of FIG. 7B. In the illustrated example clasp assembly 663A is made up of an overhang 664A mounted to an outer surface of the first segment $648A_1$, and which is configured to elastically slide over a lip 666A shown on an upper outer surface of the base segment 650A. Lip 666A of FIG. 7B has a generally curved outer surface that projects radially outward from base segment 650A. Overhang 664A which has a generally U-shaped cross-section that flexes radially outward when moved into engaging cooperation with lip 666A, and which requires a force to disengage therefrom. The size and configuration of clasp assembly 663A is strategically formed so that the force FR is less than a force that would deform components of the guard assembly 644A.

In an example of use of the needle system 610A and guard assembly 644A, an open end of base segment 650A is mounted to hub 634A thereby covering shaft 636A and bevel 638A. First segment $648A_1$ is retracted by applying Force $F_R$ as illustrated in FIG. 7A; and which exposes a shaft 636A to a designated penetration $D_P$ distance. Bevel 638A is put into contact with an outer surface of subject and shaft 636A is inserted into subject up to the designated penetration $D_P$ distance. After removing shaft 636A from subject, first segment $648A_1$ is pivoted back to its deployed configuration of FIG. 7A, which blocks contact between the bevel 638A and unintended subjects. Pivoting first segment $648A_1$ back to the deployed configuration allows for the safe disposal of the needle assembly 632A.

Figure 8A:
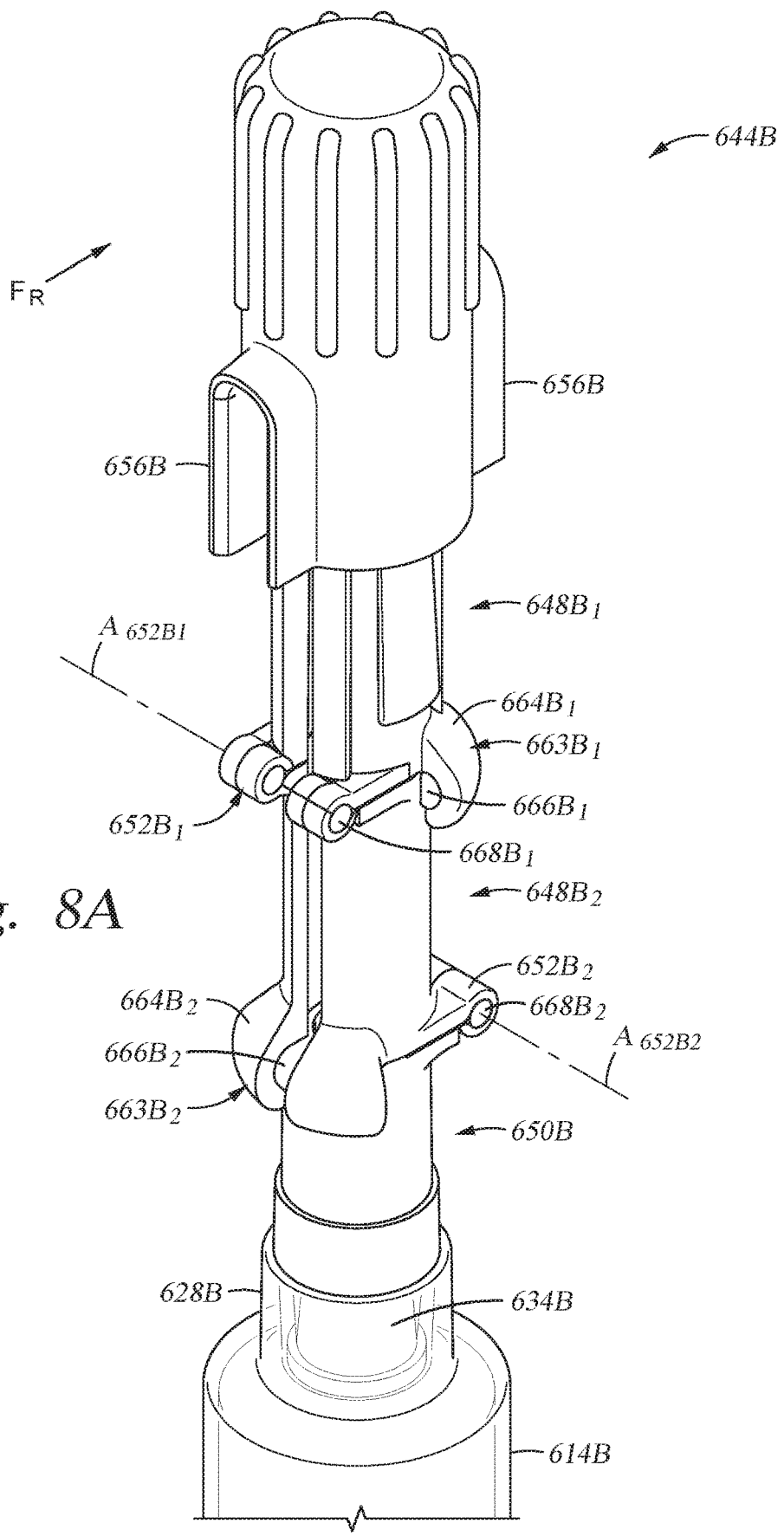
FIG. 8A is a perspective view of an embodiment of the multiple-length guard assembly of FIG. 6 in a neutral configuration.
Figure 8B:
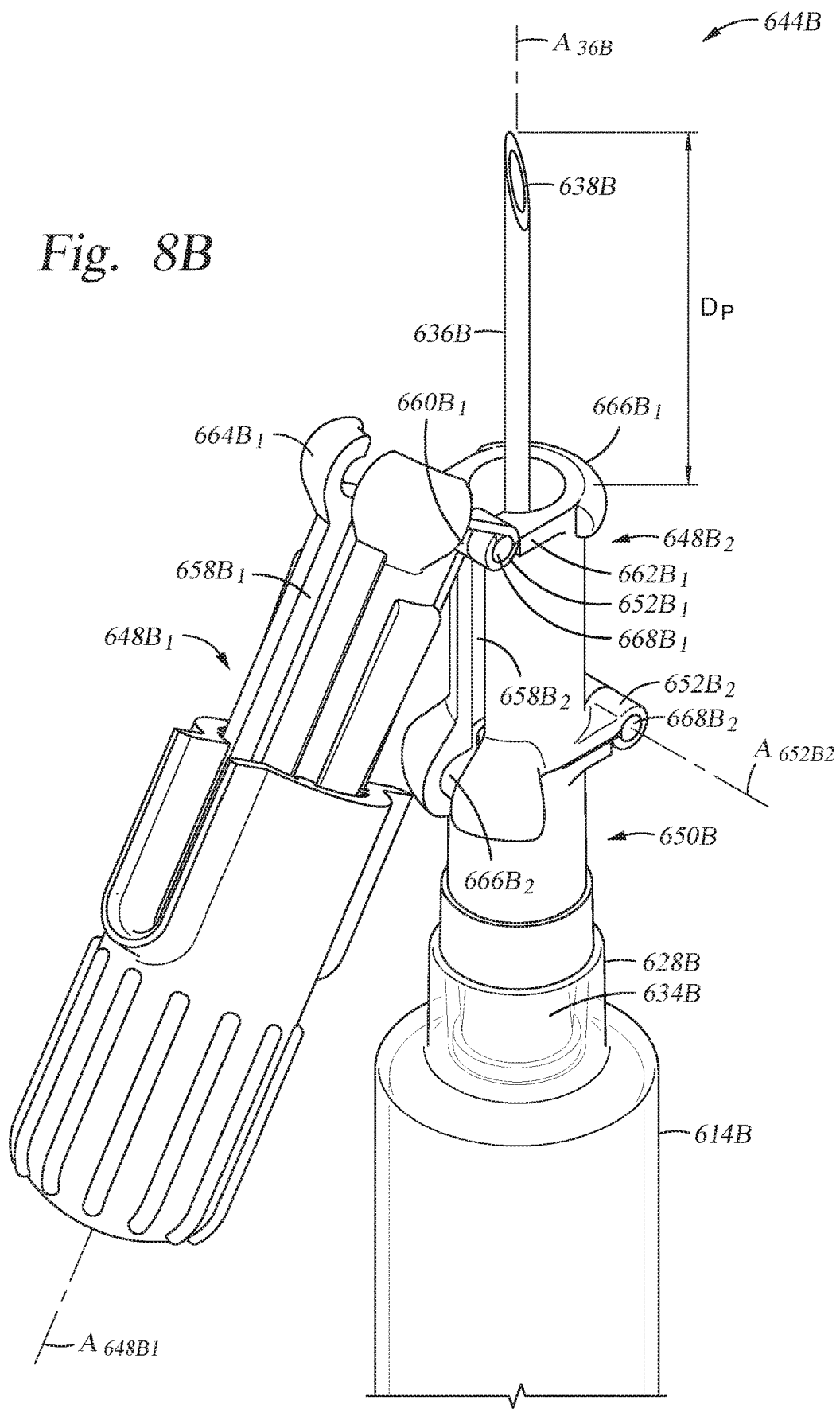
FIGS. 8B and 8C are perspective views of the guard assembly of FIG. 8A in a retracted configuration.
Figure 8C:
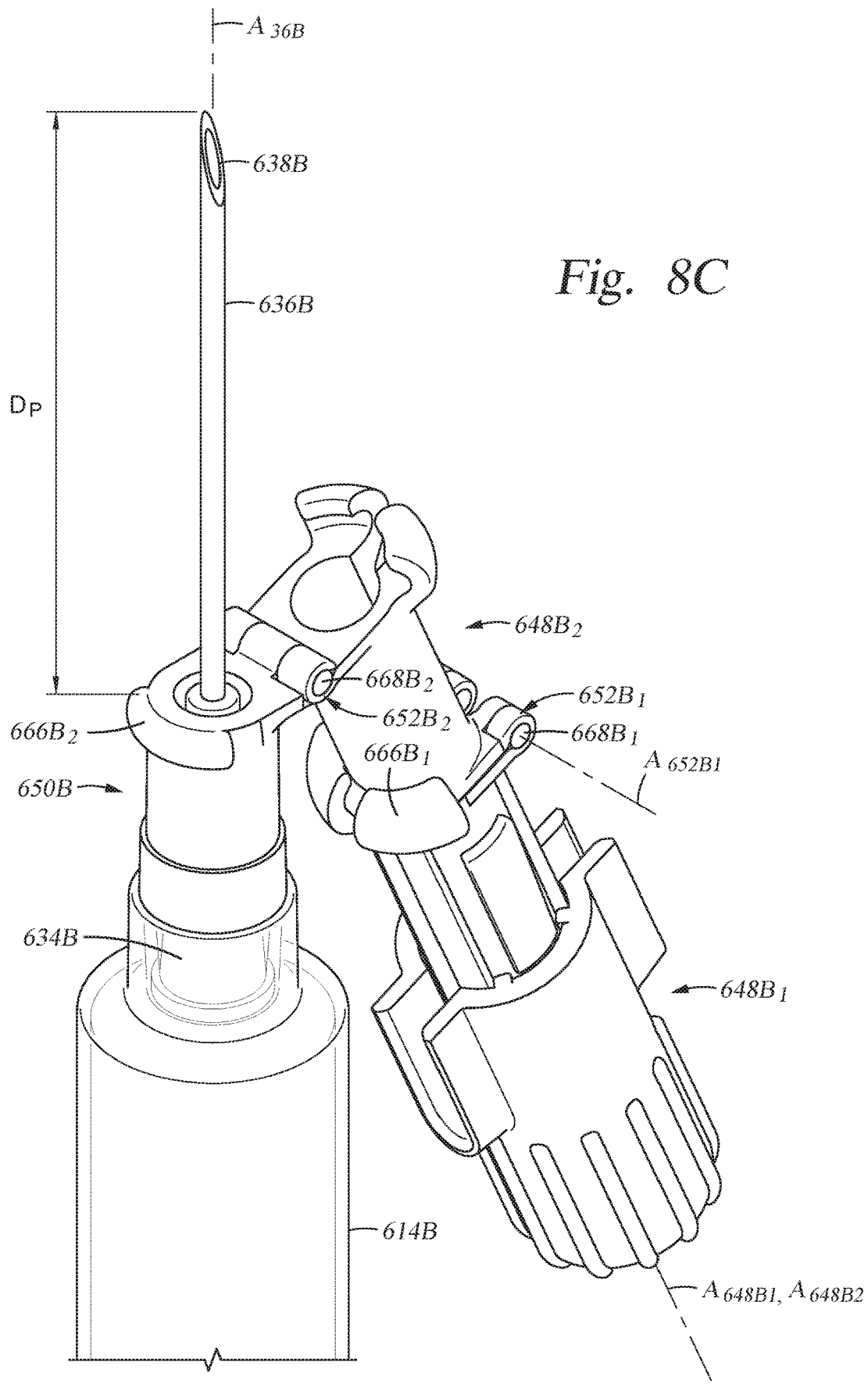

Shown in a perspective and partial side sectional views in FIGS. 8A through 8C is an embodiment of the guard assembly 644B having first and second segments $648B_1$, $648B_2$ which are coupled to one another, and also coupled to a base segment 650B. In this example, the first segment $648B_1$ is pivotingly coupled to second segment $648B_2$ via a hinge assembly $652B_1$ and clasp assembly $663B_1$, and where the second segment $648B_2$ is coupled with base segment 650B by a hinge assembly $652B_2$ and clasp assembly $663B_2$. Further in this example, and as depicted in FIG. 8B, is that hinge assembly $652B_1$ includes leaves $660B_1$, $662B_1$ that are coupled to one another via a pin $668B_1$. Further in this example is that the first segment $648B_1$ is pivotingly retracted with respect to the second segment $648B_2$, and about pin $668B_1$. In an example, shaft 636B is inserted into a subject when first segment $648B_1$ in the retracted mode and coupled to second segment $648B_2$. Further in this example, when shaft 636B is removed from subject the first segment $648B_1$ is returned to its deployed configuration of FIG. 8A to provide a protective and prophylactic barrier from contact with bevel 638B after shaft 636B has penetrated the subject. Further illustrated in FIG. 8A, is that the pin $668B_1$ is along the axis $A_{652B1}$, an orientation different from that of pin $668B_2$ which is along axis $A_{652B2}$. As such, embodiments exist where the segments $648B_1$, $648B_2$ are oblique, transverse, or parallel with one another when in their respective retracted modes. Alternatively, as shown in FIG. 8C, first and second segments $648B_1$, $648B_2$ are each along axes $A_{648B1}$, $A_{648B2}$ that are generally coaxial with one another. Retracting second segment $648B_2$ yields a penetration depth $D_P$ greater than that when only segment $648B_1$ is in the retracted mode. In the example of FIGS. 8A-8C, a large range of penetration depths is possible with the configurations illustrated herein. As the segments $648B_1$, $648B_2$, 650B remain coupled to one another irrespective if segments $648B_1$, $648B_2$ are retracted or deployed, moving segments $648B_1$, $648B_2$ back to the deployed mode maintains a barrier over bevel 638B irrespective of the particular penetration depth $D_P$ that is ultimately achieved. An example of use of the embodiments of FIGS. 8A-8C is similar to that of the embodiments of FIGS. 7A and 7B, with the added option of retracting and redeploying the second segment $648B_2$.

Figures 9A, 9B:
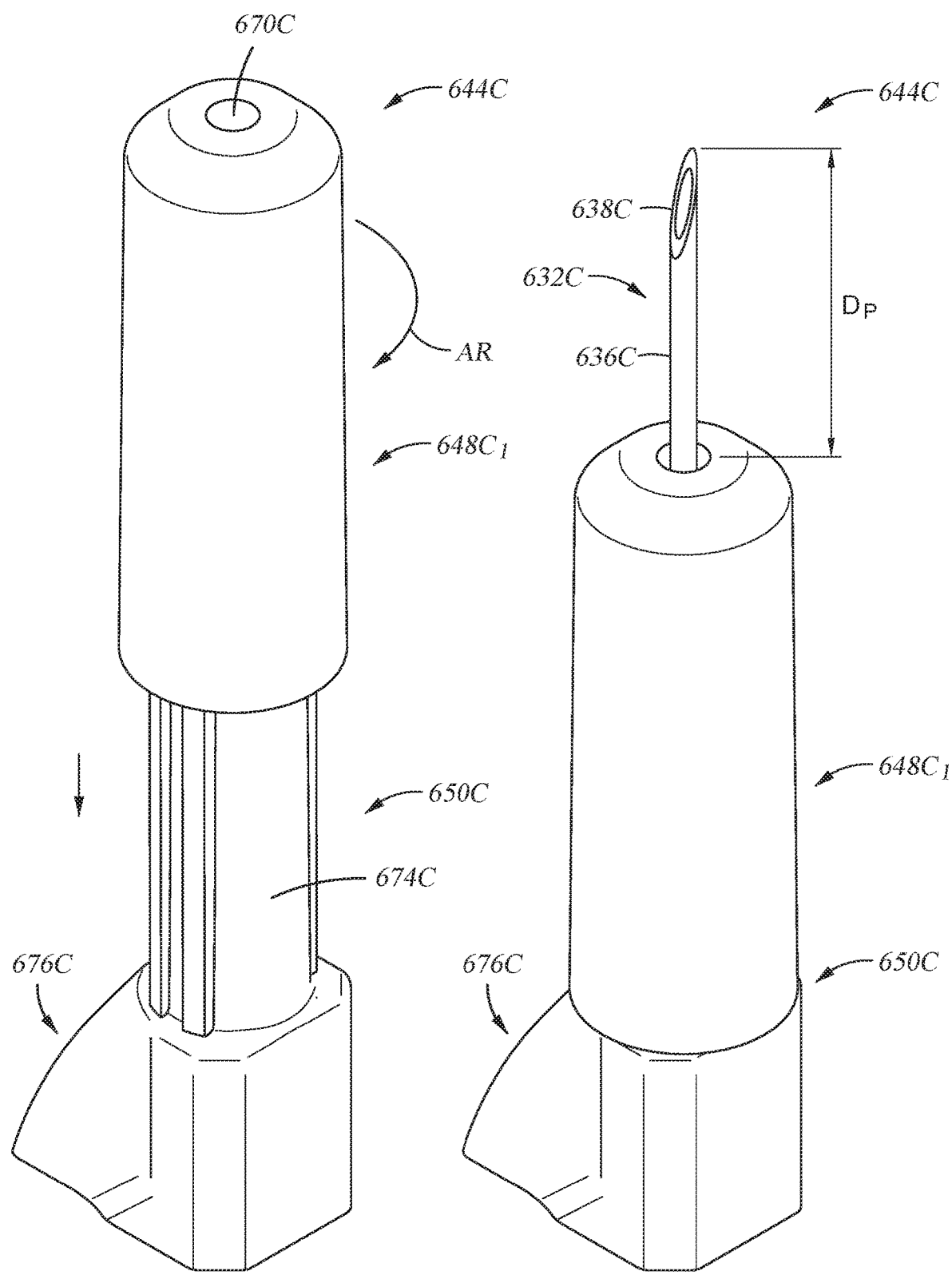
FIGS. 9A and 9B are perspective views of an embodiment of the guard assembly of FIG. 6 in a locked and retracted configuration respectively.
Figures 9C, 9D:
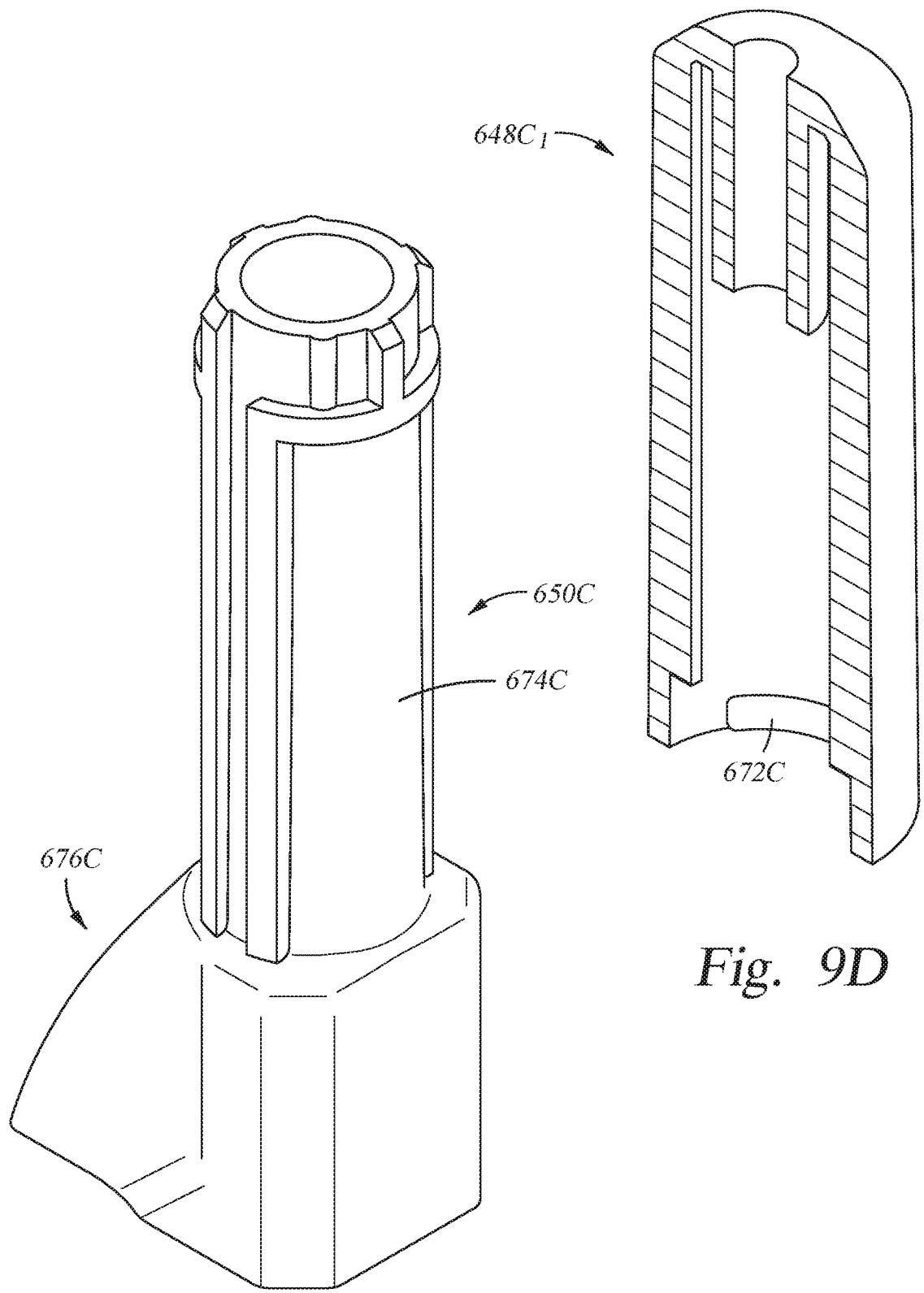
FIG. 9C is a perspective view of a base segment of the guard assembly of FIG. 9A.
FIG. 9D is a perspective sectional view of a first segment of the guard assembly of FIG. 9A FIGS. 10A and 10B are perspective views of an embodiment of the guard assembly of FIG. 6 in a locked and retracted configuration respectively.

Another alternate embodiment of the guard assembly 644C is provided in FIGS. 9A-9D, where in FIG. 9A the guard assembly 644C is shown in a perspective view having a first segment $648C_1$ that is axially moveable with a base segment 650C. An aperture 670C is shown formed on an end of first segment $648C_1$ distal from segment 650C, and as depicted in FIG. 9B, provides for a way to allow passage of shaft 636C when the first segment $648C_1$ is moved axially with respect to base segment 650C as shown in FIG. 9B. Guard assembly 644C in a retracted configuration in the example of FIG. 9B. Referring to FIGS. 9C and 9D, base segment 650C is shown in perspective view, and first segment 648C$_1$ is in a perspective sectional view. A tab 672C is provided that projects radially inward from an inner surface of first segment 648C$_1$. When first segment 648C$_1$, and thus tab 672C, is in a particular azimuthal orientation, tab 672C aligns and interferes with an outer shoulder of base segment 650C. Interfering contact between tab 672C and shoulder of the base segment 650C blocks axial movement of first segment 648C$_1$ with base segment 650C. An axial recess 674C is shown formed at a particular circumferential location along base segment 650C. Tab 672C aligns with recess 674C by rotation of first segment 648C$_1$ as shown by the arrow of rotation A$_R$. When aligned with recess 674C, tab 672C is not in interfering contact with shoulder, and the first segment 648C$_1$ is axially moveable into the retracted configuration of FIG. 9B. As shown, shaft 636C is exposed a distance for a penetration depth D$_P$. Guard assembly 644C is selectively reconfigured into the deployed configuration of FIG. 9A by axially moving first segment 648C$_1$ so that tab 672C is past shoulder, and rotating first segment 648C$_1$ so that tab 672C is in interfering contact with shoulder. Hinge 676C is one example of a hinge included with the SafetyGlide™ syringe obtainable from Becton Dickinson, 1 Becton Drive, Franklin Lakes, NJ 07417 (www.bd.com). It should be pointed out that which is provided in the present disclosure is adaptable to accommodate any type of needle assembly or syringe, including those with safety mechanisms. In an alternative, first segment 648C$_1$ slidingly mounts directly onto syringe, and is moveable along the length of syringe to expose needle 636C and/or to adjust a depth of penetration D$_P$.

Figures 10A, 10B:
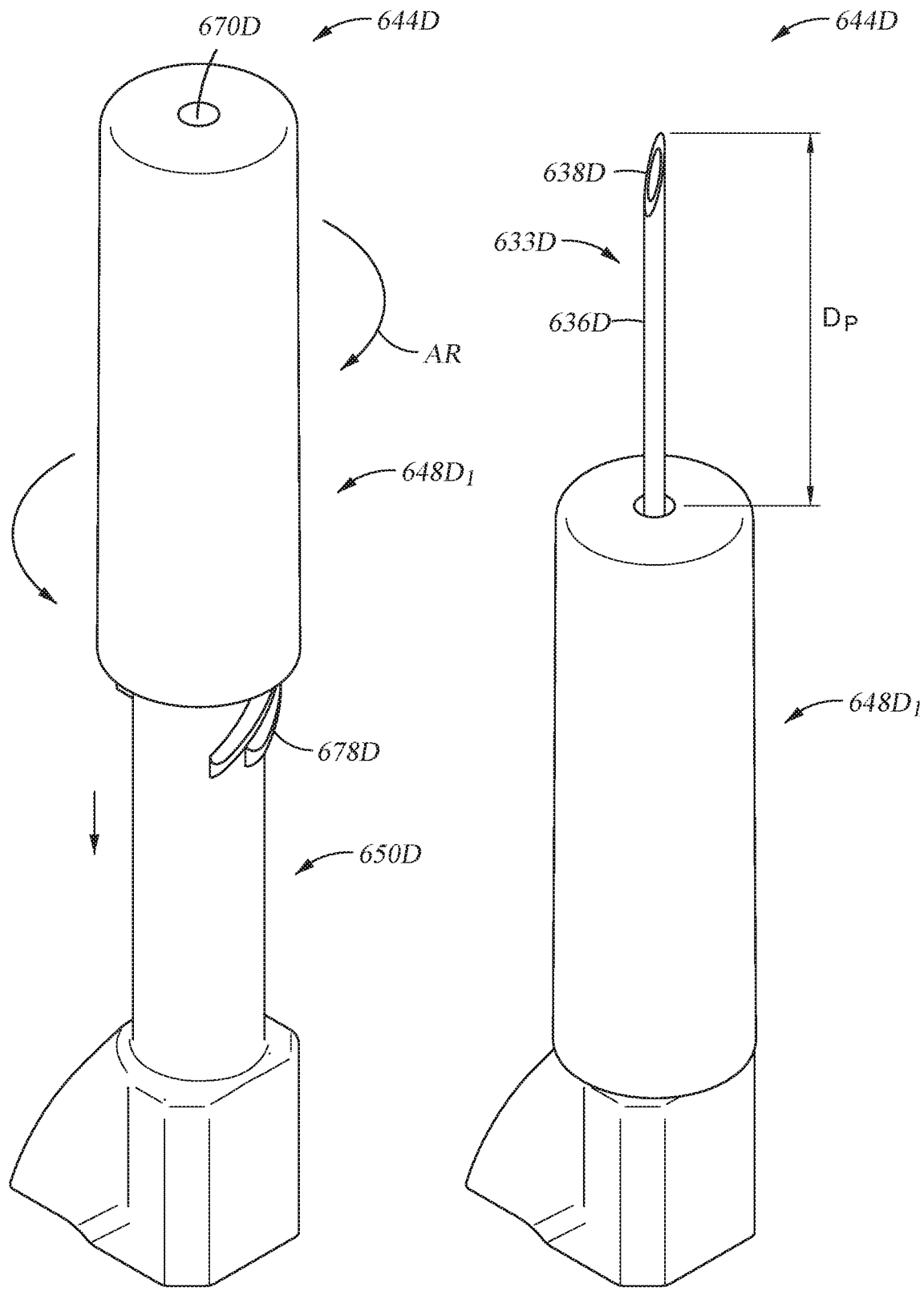
FIG. 10C is a perspective view of a base segment of the guard assembly of FIG. 10A.
FIG. 10D is a perspective sectional view of a first segment of the guard assembly of FIG. 10A.
Figures 10C, 10D:
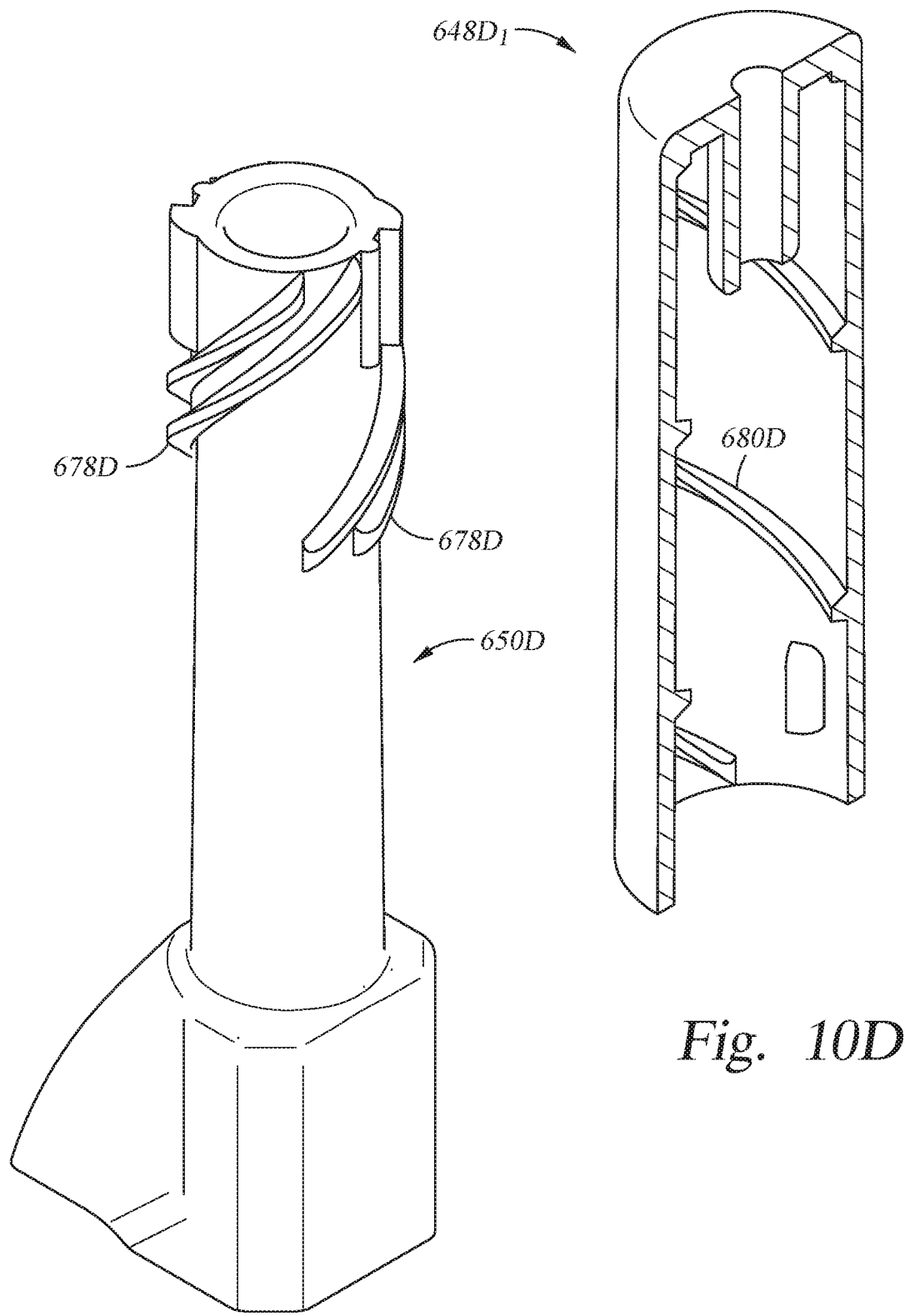

Another embodiment of guard assembly 644D is illustrated in FIGS. 10A-10D, and where the first segment 648D$_1$ is axially moveable with respect to the base segment 650D to put the assembly 644D into a retracted mode with shaft 636D exposed a distance for a penetration depth D$_P$. Shown in FIGS. 10A, 10C are threads 678D formed on an outer surface of the base segment 650D. In FIG. 10D first segment 648D$_1$ is shown in a perspective sectional view, and provided with threads 680D formed on its inner surface of the first segment 648D$_1$ that engage with threads 678D formed on an outer surface of the base segment 650D. In an example of operation, rotating segments 648D$_1$, 650D with respect to one another results in an axial movement of first segment 648D$_1$ with respect to base segment 650D thereby exposing shaft 636D. Rotating one or both segments 648D$_1$, 650D in opposite directions returns assembly 644D into the deployed configuration of FIG. 10A to draw shaft 636D back to within first segment 648D$_1$ so that the bevel 638D is prevented from contact with another subject or object. In an alternative, first segment 648D$_1$ mounts directly onto syringe with its threads 680D in engaging contact with syringe; so that rotating first segment 648D$_1$ with respect to syringe (or vice versa), moves first segment 648D$_1$ along the length of syringe to expose needle 636D and/or to adjust a depth of penetration D$_P$.

Figures 11A, 11B:
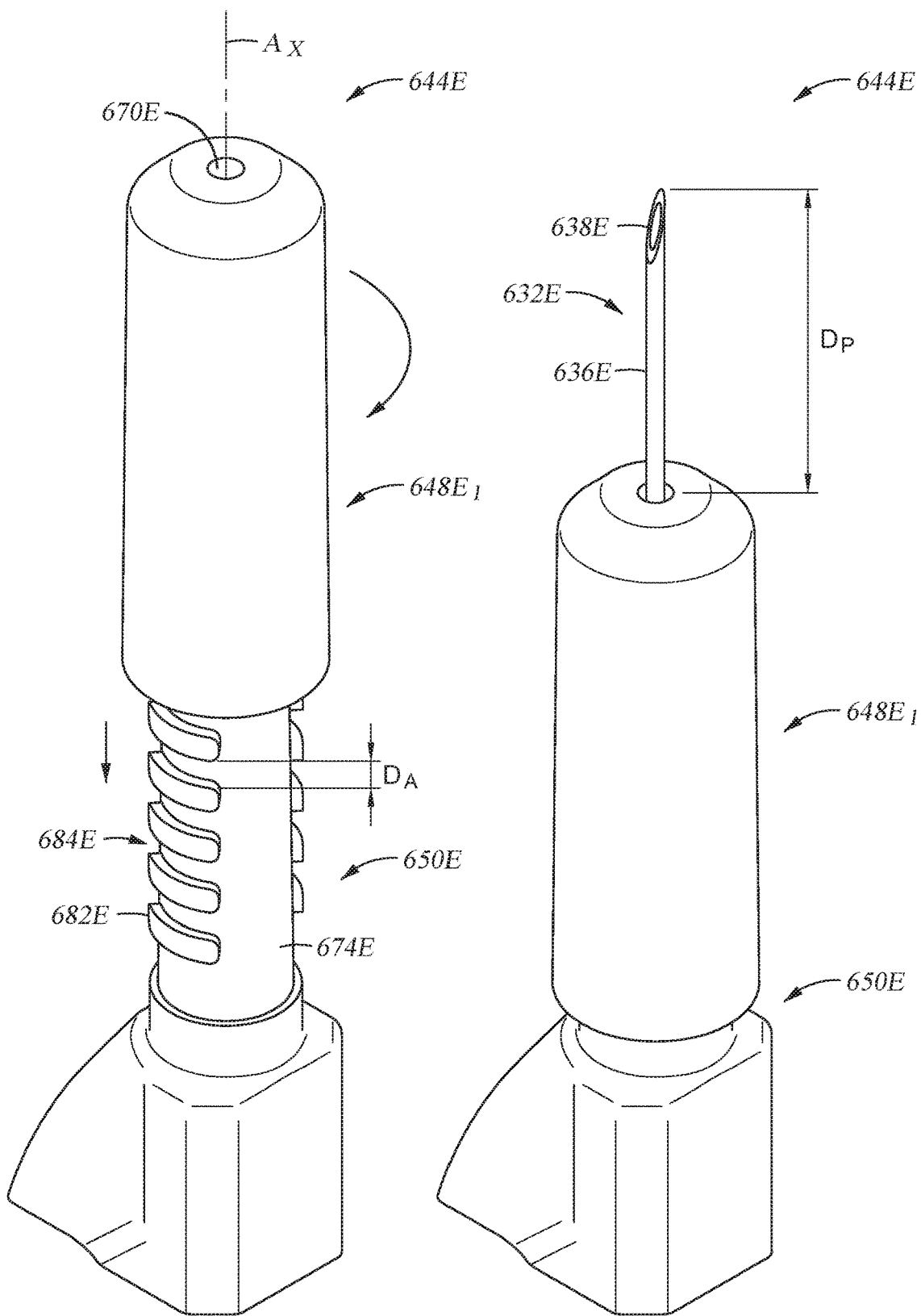
FIGS. 11A and 11B are perspective views of an embodiment of the guard assembly of FIG. 6 in a locked and retracted configuration respectively.
Figures 11C, 11D:
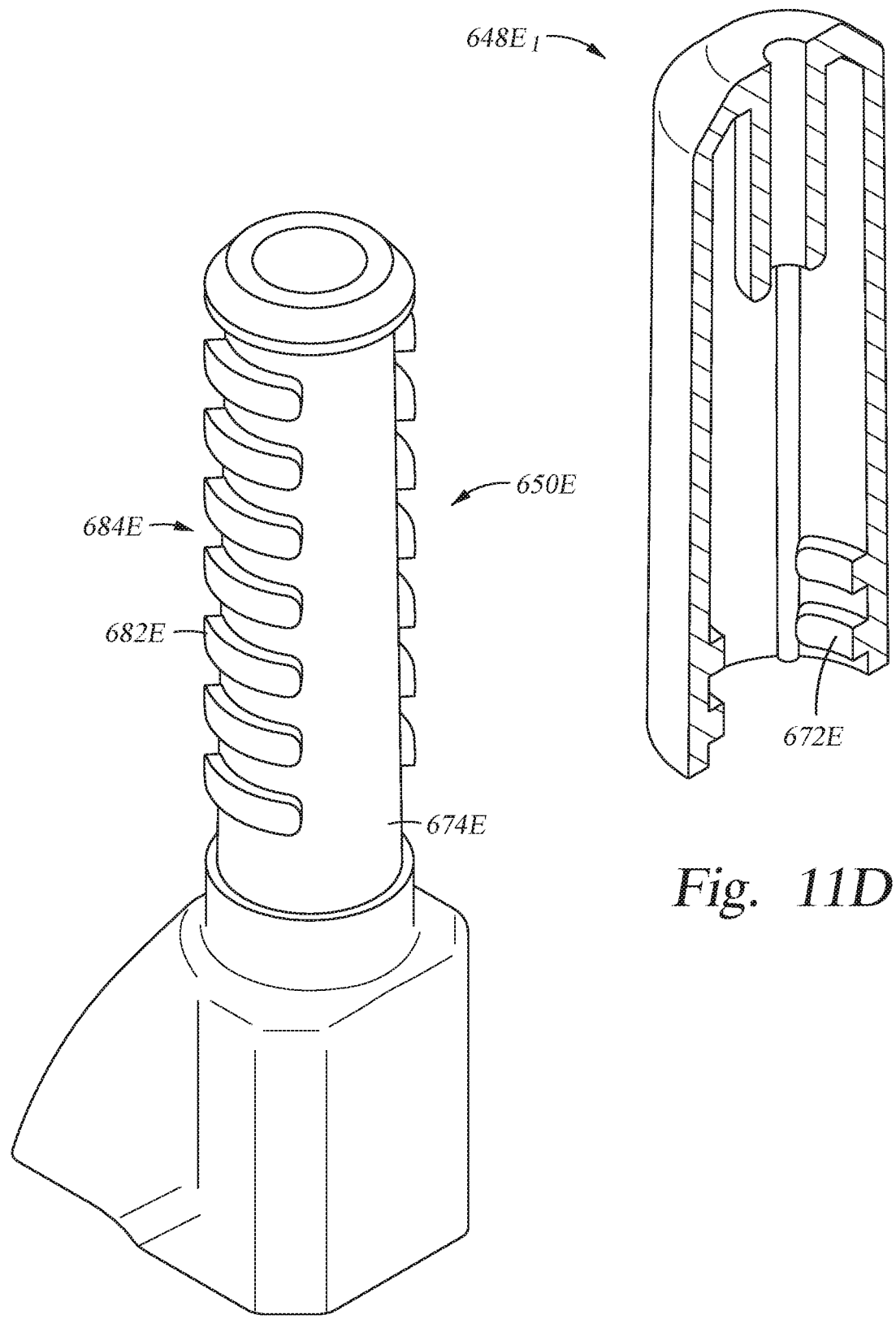
FIG. 11C is a perspective view of a base segment of the guard assembly of FIG. 11A.
FIG. 11D is a perspective sectional view of a first segment of the guard assembly of FIG. 11A.

In FIGS. 11A-11D is an embodiment of guard assembly 644E having step members 682E formed on an outer surface of base segment 650E. Shown in FIGS. 11A, 11C are step members 682E shown projecting radially outward. Depicted in perspective sectional view FIG. 11D is a first segment 648E$_1$ having a tab 672E formed on an inner surface of first segment 648E$_1$. When tab 672E is azimuthally aligned with step members 682E, and step members 682E and tab 672E are in interfering contact, which impedes axial movement of first segment 648E$_1$. Similar to the embodiment of FIGS. 9A-9D, angularly rotating first segment 648E$_1$ about its axis A$_X$ reorients tab 672E at a different azimuthal location and into selective alignment with a recess 674E formed axially along the length of base segment 650E. In the example of FIGS. 11A and 11C, the step members 682E are shown as members having a width that circumscribes a portion of the circumference of the outer surface of base segment 650E; and are elongate such that the width exceeds their height. In the example of FIGS. 11A and 11C, lateral edges of each step member 682E terminate at substantially the same azimuthal location to define the axial recess 674E. Moreover, adjacent step members 682E are spaced a distance DA apart from one another. Examples exist where distance D$_A$ is the same, and alternative embodiments exist where distance D$_A$ varies along the axial length of the step members 682E. The spacing between adjacent step members 682E defines slots 684E that selectively receive the tab 672E. Axially aligning first segment 648E$_1$, and rotating the first segment 648E$_1$, guides the tab 672E into a particular one of the slots 684E. In this example, multiple levels of retraction of the first segment 648E$_1$ are available, so that a number of different penetration depths D$_P$ are achievable with this configuration. In an alternate embodiment, step members 682E are provided onto syringe allowing first segment 648E$_1$ to be mounted directly onto syringe so that selective axial movement of first segment 648E$_1$ exposes/covers needle 636E and also adjusts penetration depth D$_P$. In yet another alternative, first segment is an annular member that telescopingly mounts to an outer surface of syringe. In this alternate embodiment, inner walls of the first segment and outer surface of syringe are substantially smooth and without added profile to allow the first segment to slide along the length of the syringe. Further in this embodiment, the inner surface of the first segment and outer surface of the syringe are in close contact so that an applied force is required to slide the first segment with respect to the syringe, which hinders movement of the first segment due to gravity forces alone.

Figures 12A, 12B:
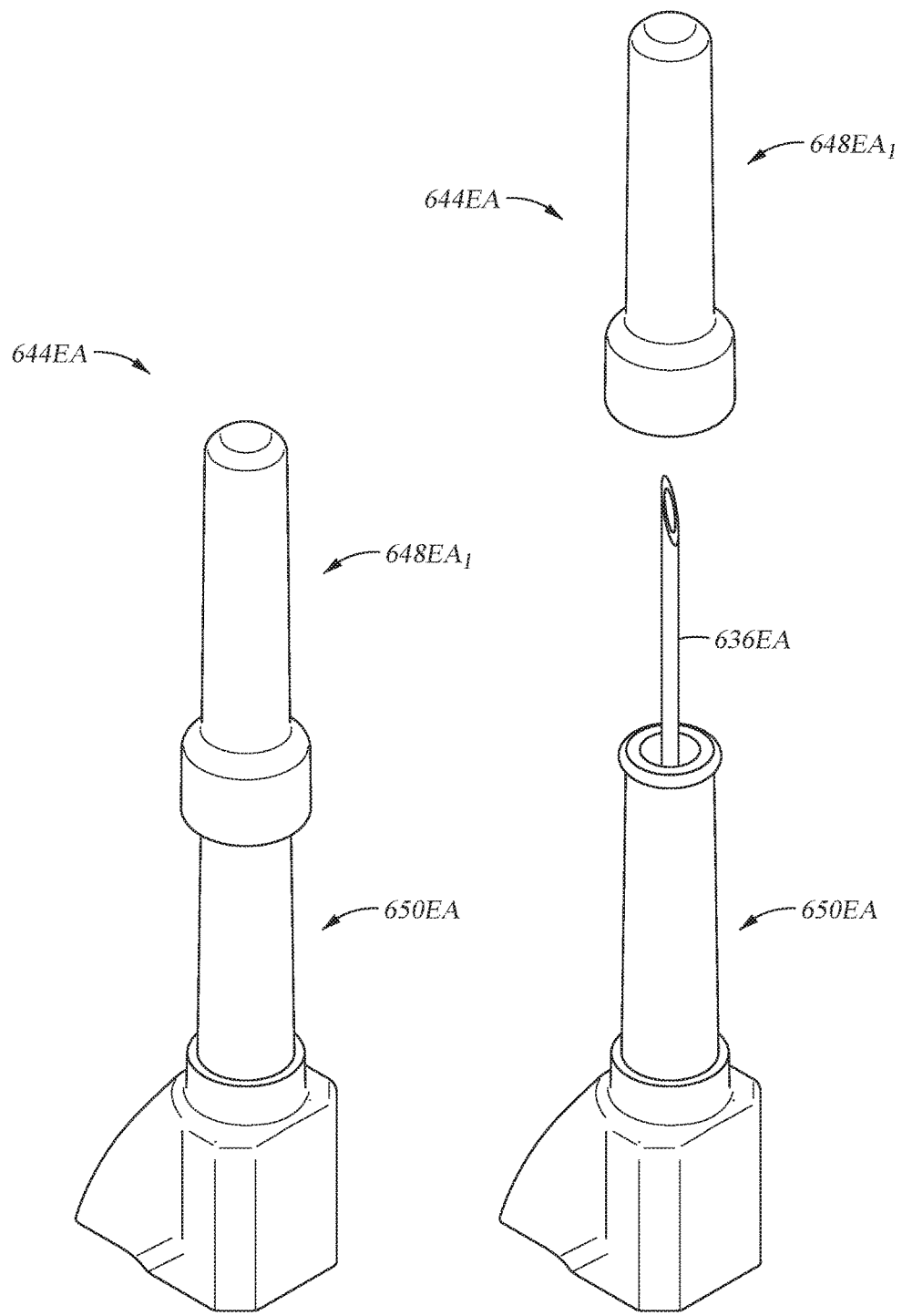
FIGS. 12A and 12B are perspective views of an alternate embodiment of a guard assembly.

In FIGS. 12A and 12B an example of a guard assembly 644EA is shown in a perspective view. In this example, first segment 648EA$_1$ slidingly mounts to base segment 650EA, and as shown in FIG. 12B and illustrated by arrow, first segment 648EA$_1$ is totally detachable from base segment 650EA by moving first segment 648EA$_1$ in a direction away from base segment 650EA. Respective ends of segments first segment 648EA$_1$, 650EA are flared to different diameters, so that an end of one having the smaller diameter (shown as the upper end of base segment 650EA in FIG. 12B) inserts into the end of the larger diameter end (the lower end of first segment 648EA$_1$). Examples exist where the larger diameter end is on the base segment 650EA and vice versa. In an example, after inserting and then removing the needle shaft 636EA from a subject, the first segment 648EA$_1$ is reapplied over needle shaft 636EA. Close contact between the flared ends of the segments 648EA$_1$, 650EA provides sufficient force to prevent inadvertent removal of first segment 648EA$_1$ from base segment 650EA until needle assembly and attached guard assembly are disposed.

Figure 13A:
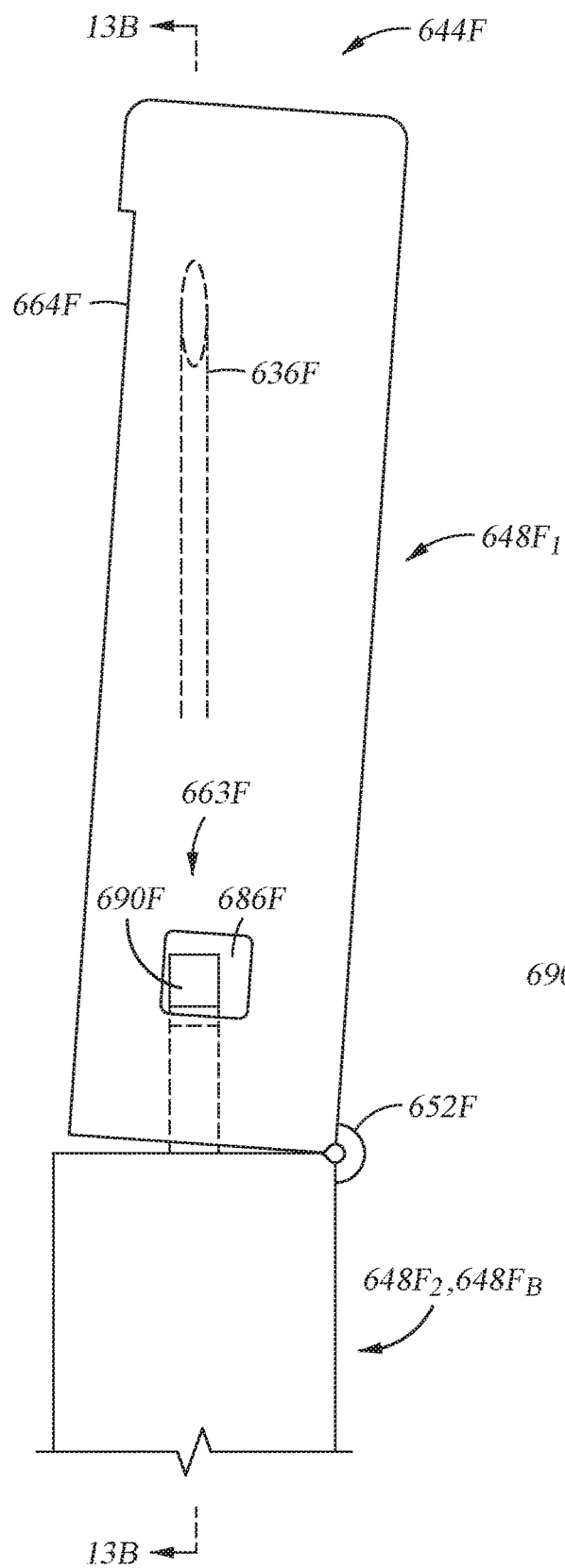
FIGS. 13A and 13B are respective lateral and anterior views of an embodiment of the guard assembly of FIG. 6 of a locking mechanism in a neutral configuration.
Figure 13B:
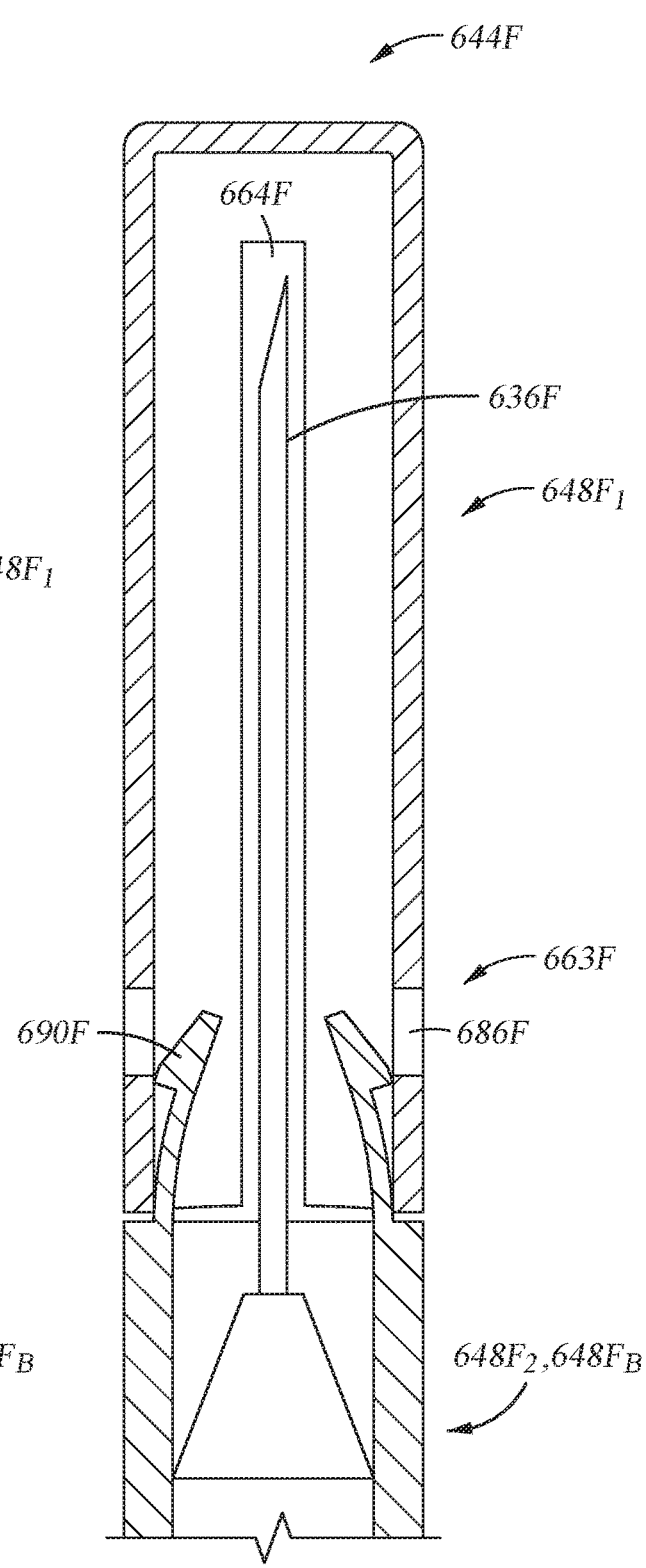
Figures 13C, 13D:
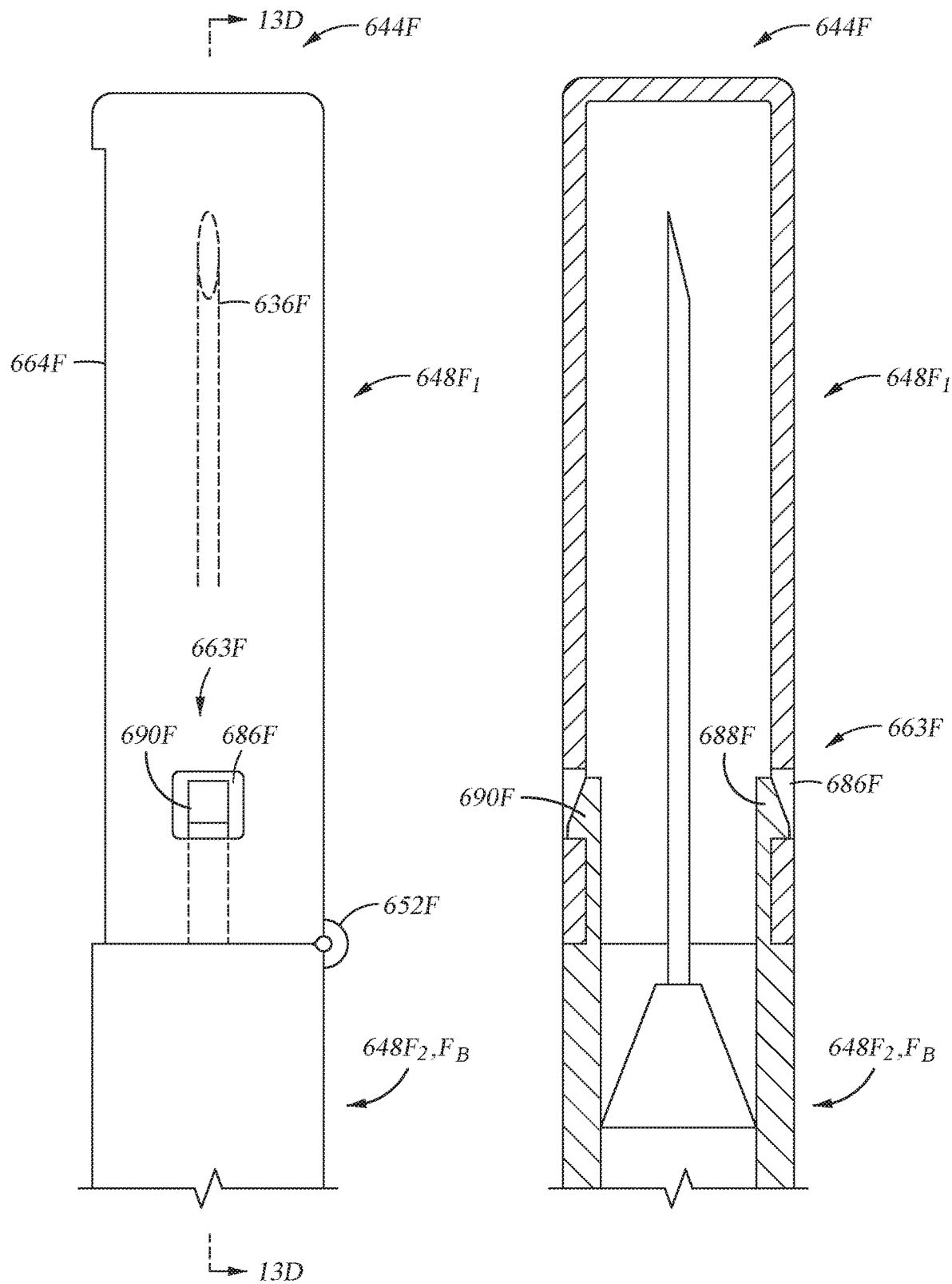
FIGS. 13C and 13D are respective lateral and anterior views of an embodiment of the guard assembly of FIG. 6 of a locking mechanism in a locked configuration.

Schematically illustrated in FIGS. 13A through 13D are alternate examples of a guard assembly 644F having a clasp assembly 663F for securing the first segment 648F$_1$ with either second segment 648F$_2$ or base segment 648F$_B$. Shown in FIGS. 13A through 13D are openings 686F through a sidewall of first segment 648F$_1$. In a lower one of the segments, i.e., 648F$_{2-n}$ or 648F$_B$, is a latch member 688 which resembles a cantilevered member that is radially deformable radially inward and away from the sidewall of the first segment $648F_1$. Illustrated in FIGS. 13B and 13D is an example of a tip 690F on a free end of the latch member 688F, and having a planar surface on a side facing a fixed end of each latch member 688F. In the example depicted in FIG. 13B, when the latch members 688F are spaced away from the openings 686F, contact between an inner surface of first segment $648F_1$ and tips 690F urges latch members 688F radially inward. In the example of FIGS. 13C and 13D, first segment $648F_1$ is moved, from that of FIGS. 13A and 13B, and into a deployed from a retracted configuration. In the deployed configuration, tips 690F register with openings 686F and the cantilevered action of the latch members 688F urges the tips 690F radially outward and into the openings 686F. The planar surfaces on the bottom edges of tips 690F exert a resistive force that resists pivoting of the first segment $648F_1$ with the remaining segments $648F_2$, $648F_B$. Similar to the other embodiments described herein, when in the deployed mode (FIGS. 13C, 13D) and the first segment $648F_1$ covers a bevel (not shown) of a shaft thereby preventing contact between bevel and other unintended subjects. As with the other embodiments as well, the size of the first segment $648F_1$ may vary so that a particular penetration is achieved. After use of the needle system on which the guard assembly 644F is combined, the clasp assembly 663F allows the first segment $648F_1$ to be redeployed as shown in FIG. 13D, and to cover the bevel. Clasp assembly 663F supplies a resistive force to retain the first segment $648F_1$ in the redeployed configuration.

Figures 14A, 14B:
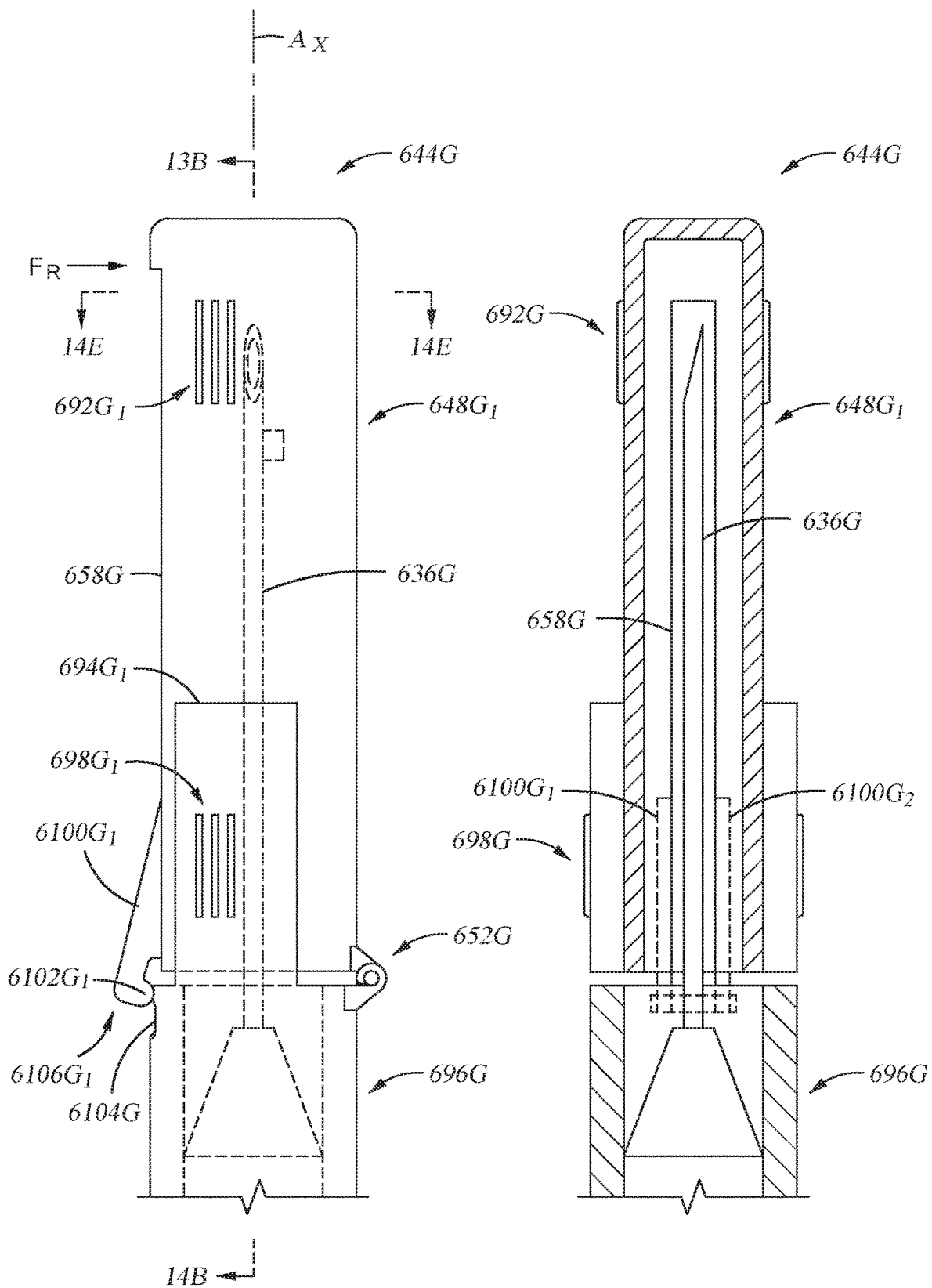
FIGS. 14A and 14B are respective lateral and anterior views of an embodiment of the guard assembly of FIG. 6 in a shipping configuration.

Referring now to FIGS. 14A and 14B, another alternate example of a guard assembly 644G is shown in side and anterior views respectively, and which includes a first segment $648G_1$ mounted onto a base segment $648G_B$. As illustrated in the embodiment of FIGS. 14A and 14B, first segment $648G_1$ is coupled to base segment $648G_B$ about hinge assembly 652G; which includes barrels mounted respectively onto the segments $648G_1$, $648G_B$, and pins inserted into the barrels. Further in this example, grooves 692G are shown formed onto lateral sides of first segment $648G_1$ and extending generally parallel with axis $A_X$ of guard assembly 644G. Grooves 692G provide surfaces on which a retracting force $F_R$ is exerted laterally onto first segment $648G_1$ for pivoting first segment $648G_1$ about hinge assembly 652G. In this example, base segment $648G_B$ includes spaced apart semi-circular sidewalls $694G_{1,2}$ (FIG. 14E) that project axially from pedestal 696G. Grooves 698G are also provided on the outer lateral surfaces of sidewalls $694G_{1,2}$ to provide a surface for exerting a force that can oppose the force applied to grooves 692G.

Shown in a side view in FIG. 14C is an example of guard assembly 644G in a retracted configuration and with first segment $648G_1$ pivoted about hinge assembly 652G; shaft 636G is exposed when guard assembly 644G is in the retracted configuration. Similar to the embodiments described above, shaft 636G passes through slot 658G (shown in dashed outline in FIG. 14B) while the first segment $648G_1$ pivots about hinge assembly 652G. Anterior terminal ends of sidewalls $694G_{1,2}$ are spaced apart from one another to define a gap 699G (FIGS. 14C and 14E) in which first segment $648G_1$ enters when it is put into the retracted mode of FIG. 14C; and that allows first segment $648G_1$ to pivot past the upper ends of sidewalls $694G_{1,2}$.

Referring back to FIG. 14A, a male latch tab 6100G is shown formed on a forward surface of first segment $648G_1$. The example of male latch tab 6100G of FIG. 14A extends axially past an upper surface of base segment $648G_B$, and has a width (defined radially from axis $A_X$) that increases with distance towards pedestal 696G. A protrusion 6102G is formed on a terminal end of male latch tab 6100G that projects radially inward towards pedestal 696G. In the neutral or shipping configuration illustrated in FIG. 14A, protrusion 6102G inserts into a recess 6104G formed into a forward surface of pedestal 696G. Engaging protrusion 6102G and recess 6104G defines a shipping latch 6106G for retaining first segment $648G_1$ in the shipping or neutral configuration. A forward gap 6107G is formed in the space between the forward terminal ends of sidewalls $694G_{1,2}$, and in which inserts male latch tab 6100G when protrusion 6102G engages recess 6104G. In an example of operation, moving protrusion 6102G out of engagement with recess 6104G, such as by pivoting of first segment $648G_1$ with respect to base segment $648G_B$, deforms male latch tab 6100G; the amount of retracting force $F_R$ required to move protrusion 6102G from recess 6104G is dependent on the respective configurations of the protrusion 6102G and recess 6104G, as well as the modulus of elasticity of the material making up the male latch tab 6100G. It is within the capabilities of one skilled to design profiles of the protrusion 6102G and recess 6104G, and to select material for the male latch tab 6100G; so that the retracting force $F_R$ required to pivot the first segment $648G_1$ exceeds forces expected during shipping and handling, so that the first segment $648G_1$ remains in place to cover the shaft 636G until the retracting force $F_R$ is deliberately applied for pivoting first segment $648G_1$ into a retracted configuration as depicted in FIG. 14C. Examples exist where guard assemblies described herein are mounted to a corresponding needle assembly at a facility where needle assembly is manufactured, and remain mounted to needle assembly during shipping, distribution, storage, usage, and disposal. An advantage of the guard assemblies described is that covers specifically for covering the needle assembly during shipping are not required.

An example of a locking tab 6108G is shown projecting radially inward from an inner surface of first segment $648G_1$. As illustrated in the plan view of FIG. 14E, locking tab 6108G has a length that extends radially past shaft 636G. Further illustrated is that locking tab 6108G is strategically set anterior to shaft 636G when guard assembly 644G is in the shipping configuration; and out of interfering contact with shaft 636G when first segment $648G_1$ is pivoted from the shipping or neutral configuration of FIGS. 14A and 14E and into the retracted configuration of FIG. 14C. Referring now to FIG. 14D, guard assembly 644G is shown in a locked configuration, and where first segment $648G_1$ is oriented so that its axis $A_{648G1}$ is angularly offset from axis $A_{636G}$ of shaft 636B by angle θ. In an embodiment, a locking force $F_L$ is applied to first segment $648G_1$ to put guard assembly 644G in the locked configuration. Locking force $F_L$ of this example is schematically depicted in a direction extending from anterior to forward of first segment $648G_1$, and oriented generally perpendicular to axis $A_X$. In the locked configuration, and as shown in a dashed outline in FIG. 14E, locking tab 6108G is set between shaft 636G and a forward side of first segment $648G_1$. When in the locked configuration, the locking tab 6108G and shaft 636G are respectively positioned so that they will interfere with one another when reorienting first segment $648G_1$ back to the shipping configuration of FIGS. 14A, 14B. In an alternative, a force to overcome the interfering contact between locking tab 6108G and shaft 636G exceeds both the retracting force $F_R$ and the locking force $F_L$. Optionally, the force for overcoming the interfering contact is sufficient to substantially deform shaft 636G, locking tab 6108G, or both.

In the illustrated examples of FIGS. 14A through 14D, an upper surface 6110G of pedestal 696G and lower surface 6112G of first segment 648G$_1$ are complementarily formed so that when the guard assembly 644G is in the locked configuration, an interface between the surfaces 6110G, 6112G is in a plane that is oblique with axis A$_X$. Obliquely profiling surfaces 6110G, 6112G allows first segment 648G$_1$ to rotate/pivot into the locking configuration, and angularly past the shipping configuration, without interfering contact between the first segment 648G$_1$ and pedestal 696G. Further depicted in the locked configuration of FIG. 14D is that the protrusion 6102G is moved axially past recess 6104G; in one embodiment, protrusion 6102G inserts into another recess (not shown) or male locking tab 6100G is somehow engaged with pedestal 696G to resist moving the first segment 648G$_1$ out of the locked configuration.

In FIGS. 14A-14E are alternate examples of guard assemblies disclosed in FIGS. 14A-14E, and having the same or substantially similar functionality. More specifically and shown in FIG. 14A is an example of guard assembly 644H mounted over a needle assembly 632H such that the first segment 648H$_1$ provides a protective covering over shaft 636H of needle assembly 632H. In the example of FIG. 14A, the guard assembly 644H is in what is referred to as a shipping mode or configuration. In the shipping mode shipping latch 6106H engages protrusion 6102H. As shown, an end of shipping latch 6106H depends from a lower terminal portion of a sidewall of the first segment 648H$_1$ located on a forward side of first segment 648H$_1$. Shipping latch 6106H of FIG. 14A is an elongate member having a semi-circular configuration, its end opposite where it attaches to first segment 648H$_1$ is free. Within an inner radius of the curved shipping latch 6106H, a space 6116H is defined which receives protrusion 6102H. Interference between the protrusion 6102H and shipping latch 6106H maintains the guard assembly 644H in the shipping configuration illustrated in FIG. 14A; as indicated above, a force required to disengage shipping latch 6106H from protrusion 6102H has a magnitude greater than that due to expected forces that occur during shipping or handling. Similar to that of FIG. 14A, application of a deliberate force F$_R$ to the first segment 648H$_1$ disengages the shipping latch 6106H from protrusion 6102H and thereby exposing needle shaft 636H; where a magnitude of deliberate force F$_R$ exceeds that of a force experienced by guard assembly 644H during shipping and handling.

Illustrated by arrow A$_{CW}$, the first segment 648H1 rotates about the hinge assembly 652H$_1$, which is formed by leaves 660H, 662H. Leaf 660H is shown formed on an interior lower terminal end of first segment 648H1 and which it is rotatingly coupled to leaf 662H by pin 668H. Leaf 662H is formed onto an outer surface of base segment 648H$_B$ and set radially outward from the outer surface of base 648H$_B$. An interior view of the guard assembly 644H is shown in an elevational view in FIG. 14B, and illustrating the ribs 6114H that are formed on the outer surface of the first segment 648H$_1$ and which project radially outward therefrom. Additionally, the ribs 6114H are generally elongate members extending axially along the outer side walls of first segment 648H$_1$ and in a plane perpendicular with side walls of first segment 648H$_1$. Similarly shaped wings 6114H project radially outward from lateral sides of second segment 648H$_2$. Further illustrated in FIG. 14B is that hinge assemblies 652H$_1$, 652H$_2$ are semi-integrated with one another and each rotate about the same pin 668H (FIG. 14A).

Depicted in FIG. 14C is an example of a configuration of the guard assembly 6448H where first segment 648H$_1$ has been rotated from the shipping configuration of FIG. 14A leaving the shaft 636H exposed and ready for use. In this example, second segment 648H$_2$ remains generally coaxial with shaft 636H and covering a portion of shaft 646H; the uncovered portion of shaft 646H defines a penetration distance D$_P$ for insertion of shaft 646H into a subject. A greater penetration distance D$_P$ is achievable by applying a force laterally to second segment 648H$_2$, similar to that for rotating first segment 638H$_1$, to rotate second segment 648H$_2$ about hinge assembly 652H$_2$ and into the configuration depicted in perspective view in FIG. 14D. In this example, both the first and second segments 648H$_1$, H$_2$ are rotated away from shaft 646H and thereby resulting in a penetration depth D$_P$ that is greater than that of FIG. 14C. Thus, strategic dimensioning of the axial length of one or both of the first and second segments 648H$_{1,2}$ provides for multiple penetration depths with a single mechanism so that a single guard assembly 644H is usable on a variety of subjects and having different needs.

Figure 14E:
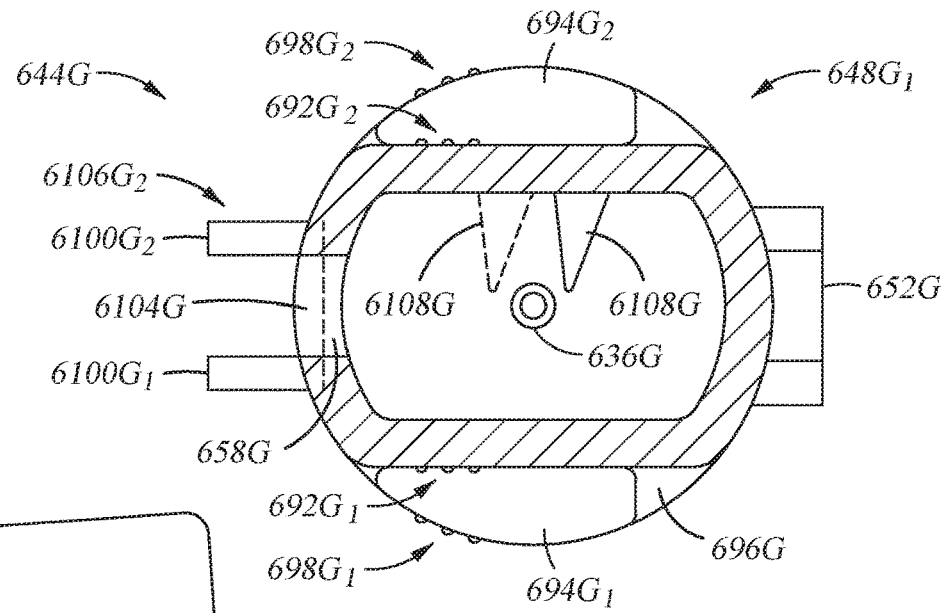
FIG. 14E is a plan view of the embodiment of the guard assembly of FIGS. 14A and 14B in a retracted configuration.
Figure 14D:
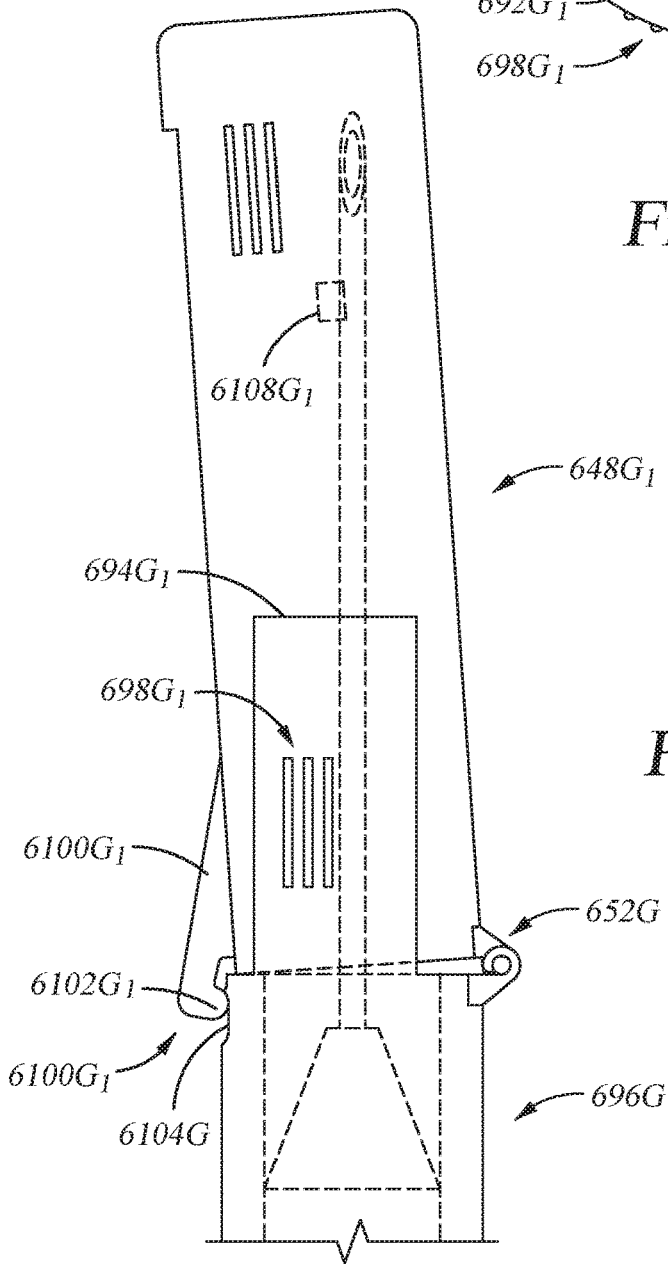
FIG. 14D is a side view of the embodiment of the guard assembly of FIGS. 14A and 14B in a locked and shipping configuration.
Figure 15A:
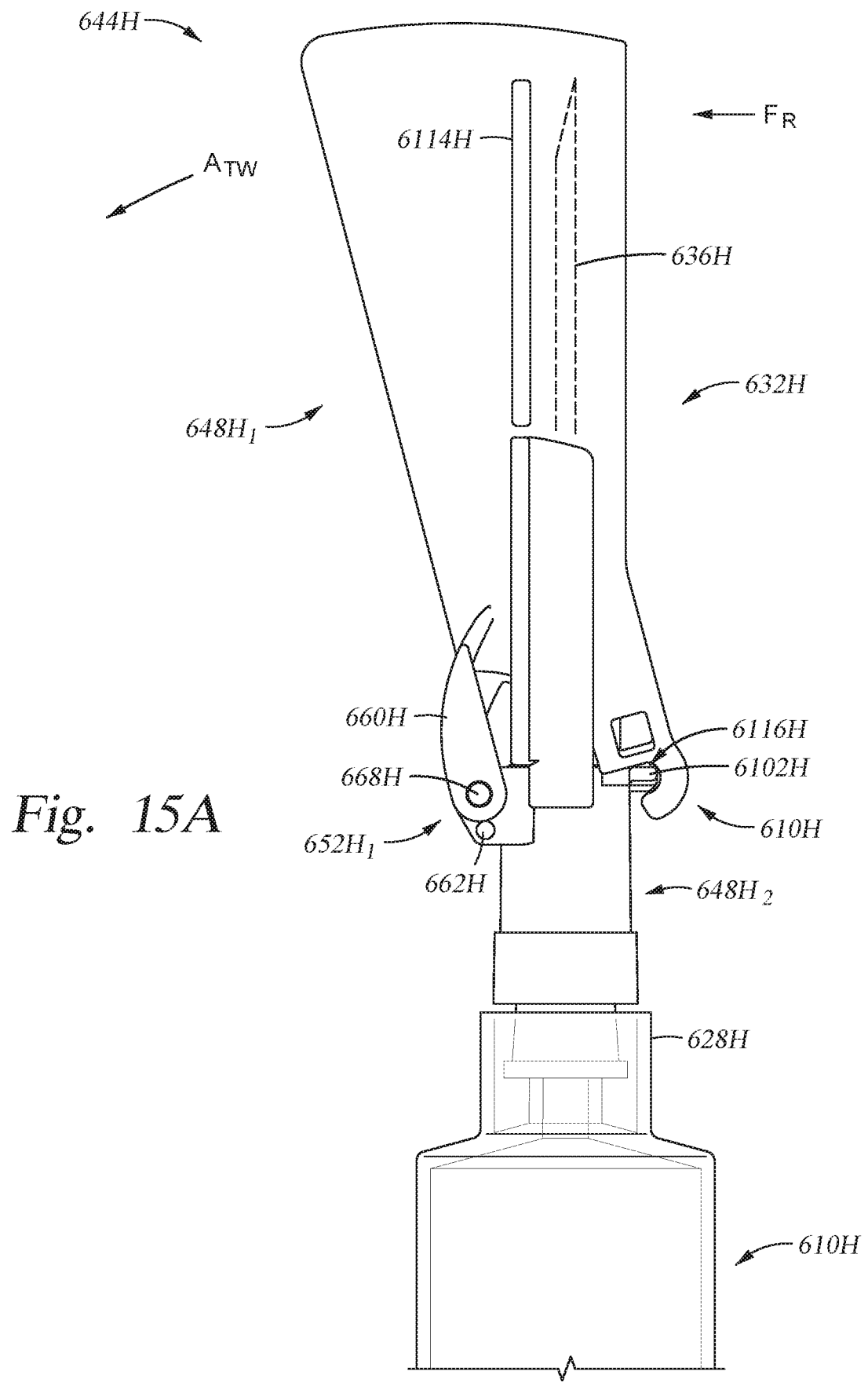
Figure 15B:
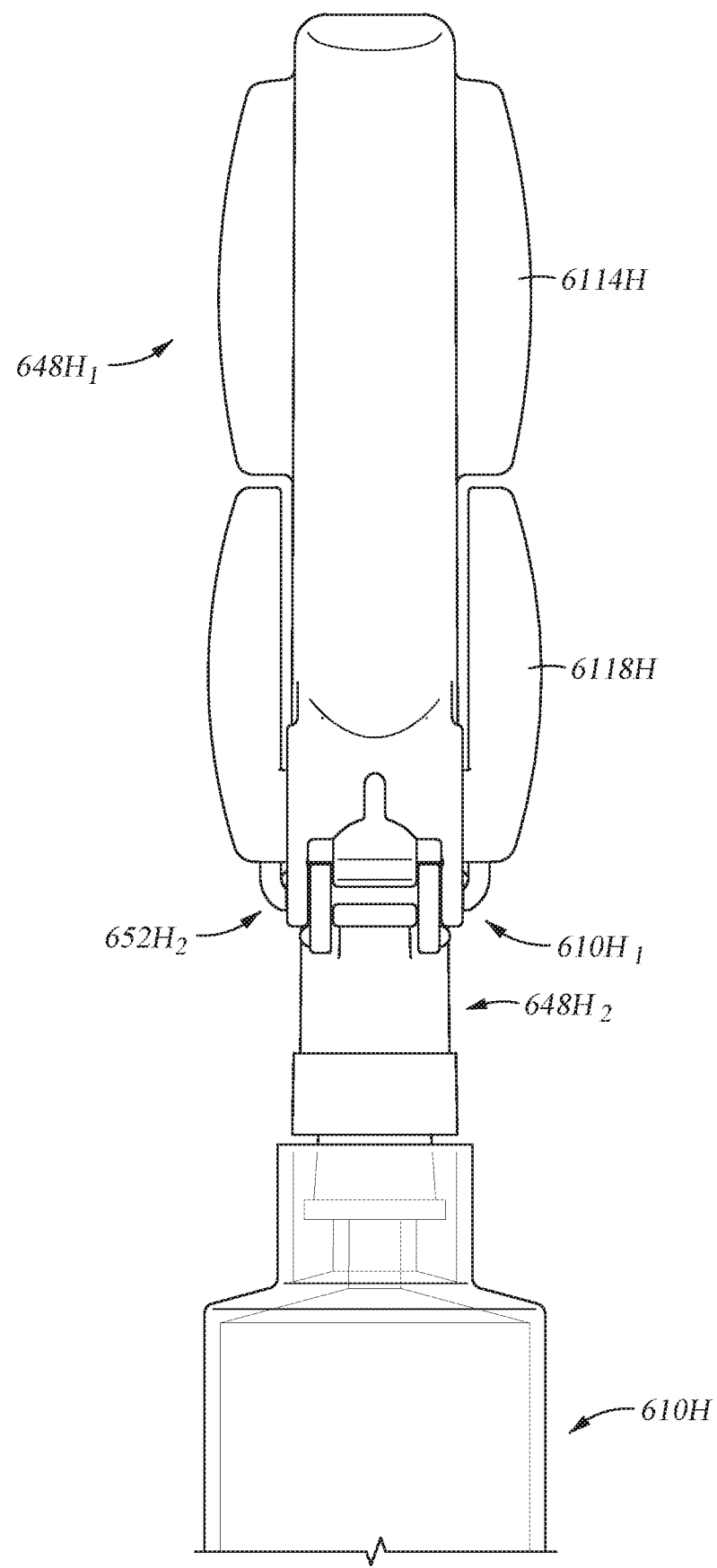
Figure 15D:
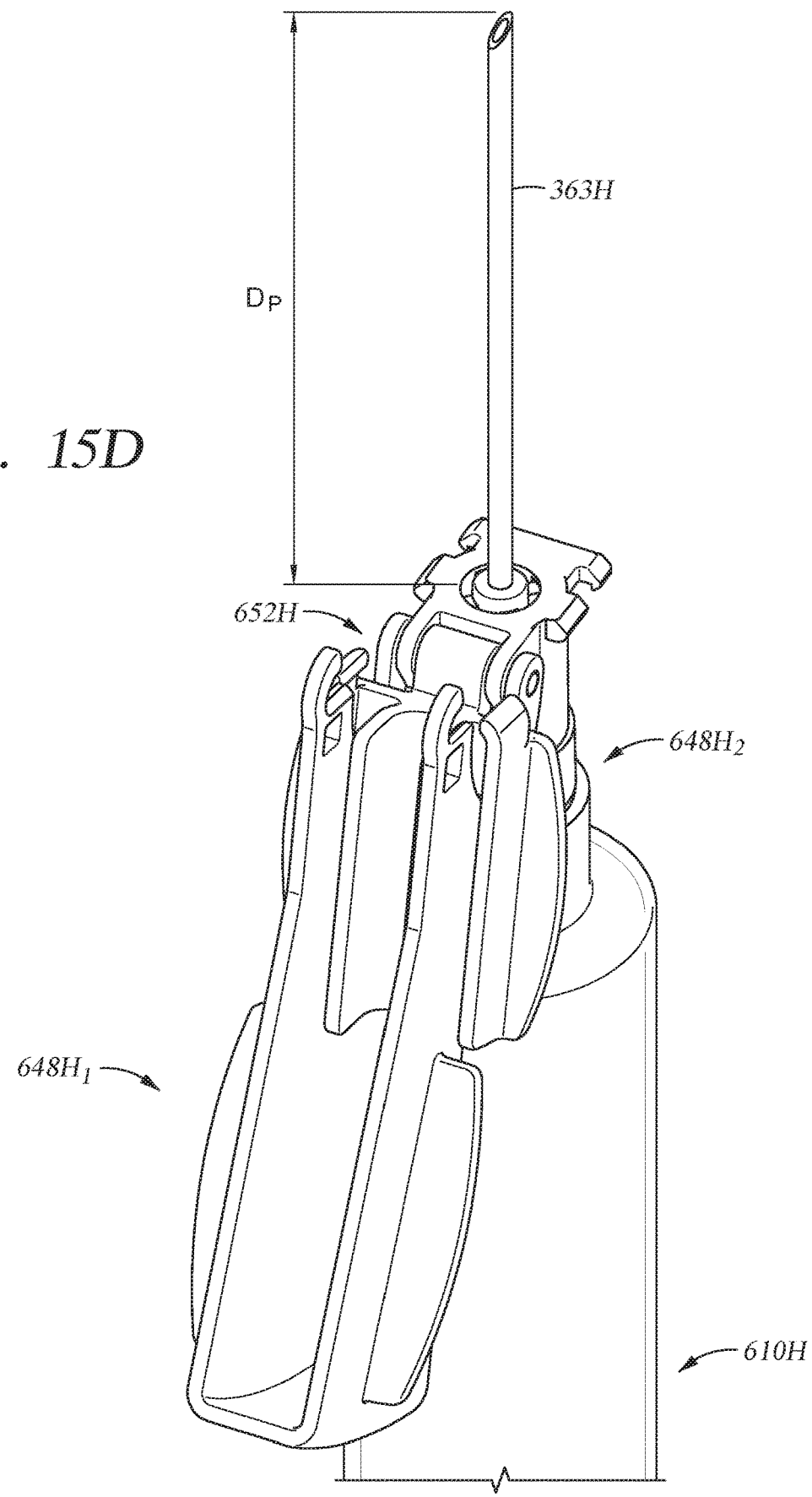
Figure 15E:
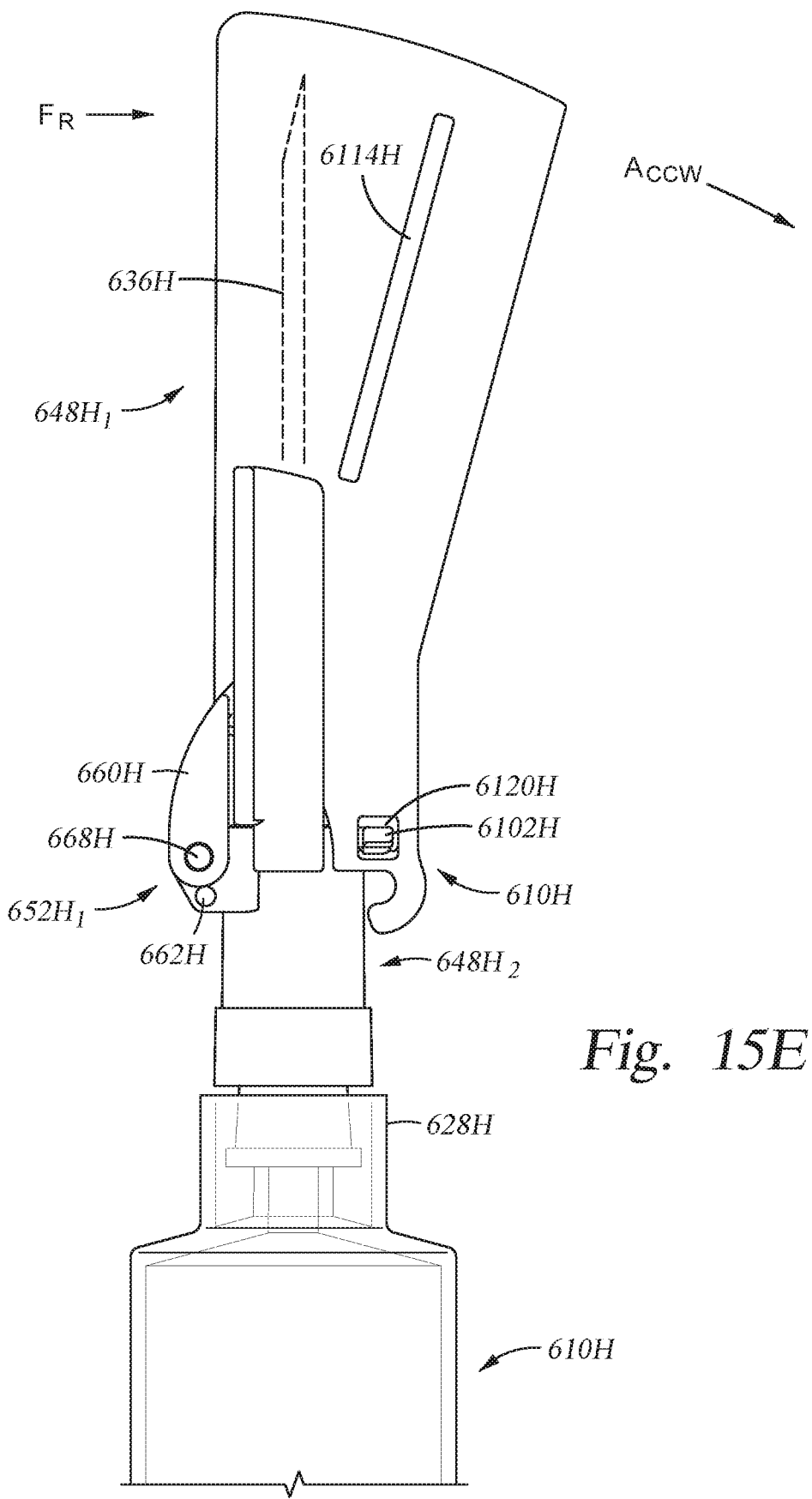

Referring now to FIG. 14E the guard assembly 644H is illustrated in a perspective view and set in what is referred to as a locked mode. In this example, first segment 648H$_1$ has been rotated about pin 668H from its position of FIG. 14 C/D, and in the direction of arrow A$_{CCW}$, and into the locked mode. Rotation of the first segment 648H$_1$ moves it into an orientation oblique to that of FIG. 14A, and as illustrated by the angled respective orientations of rib 6114H and shaft 636H; whereas in the example of FIG. 14A shaft 636H and rib 6114H are shown as being substantially parallel with one another. The travel of rotation in the direction of arrow A$_{CCW}$, and into the locked configuration of FIG. 14E, pushes the shipping latch 6106H past the protrusion 6102H and aligns protrusion 6102H with an aperture 6120H that is formed through a side wall of first segment 648H$_1$ adjacent where shipping latch 6106H joins first segment 648H$_1$. The elasticity of the respective materials making up these elements allows the protrusion 6102H to project laterally through aperture 6120H thereby maintaining the guard assembly 644H in the locked configuration of FIG. 14E. In this example, a magnitude of a force F$_{UL}$ applied to first segment 648H$_1$ sufficient to disengage protrusion 6102H with aperture 6120H exceeds magnitude of force F$_R$ sufficient to disengage latch 6106H from protrusion 6102H.

Further optionally, components of the devices illustrated in the above referenced figures and described herein, including sub-components, and/or combinations of components, are available in the form of a kit or kits for delivering or extracting materials to and from animals and humans; and where elements making up the kit or kits are within a single package or are within multiple packages. In an embodiment, a kit can contain a cap assembly and a needle system. And, the syringe is sold separately or can be fitted to syringes sold by other manufacturers. Various components of the integration unit may be sold as part of a single package or as separate packages. In other embodiments, a kit can contain a cap assembly, a needle system, and a syringe. In addition to above-mentioned components, the kits can further include instructions for using the components of the kit to practice the methods disclosed here. As such, the instructions may be present in the kits as a package insert. The instructions can be provided as part of the labeling on the kit or components thereof (i.e., associated with the packaging or sub-packaging). In other embodiments, the instructions are present as an electronic storage data file to be accessed by a user from a remote source, such as via the internet.

Those skilled in the art will recognize, or be able to ascertain using no more than routine experimentation, many equivalents to the specific embodiments of the invention described herein. Such equivalents are intended to be encompassed by the following claims. For example, embodiments exist where the guard assemblies described herein, or their equivalents, are mounted onto a corresponding needle assembly prior to being shipped to a distributer or end user; to block needle contact during shipping. Alternate embodiments exist where the guard assemblies are provided directly to a distributer or an end user, and there mounted onto a needle assembly.

The invention claimed is:

1. A cap assembly for use with a needle system, the needle system having a hub and a tip portion, the tip portion including an elongate shaft extending away from the hub, the tip portion including a bevel on a free end of the elongate shaft opposite the hub, the cap assembly comprising:
   a base segment configured to mount to the hub of the needle system;
   a first segment moveably coupled with the base segment about a first axis defined by the base segment that is oriented transverse to a longitudinal axis defined by the first segment, the first segment defining a first cavity configured to receive a portion of the elongate shaft therein; and
   a second segment moveably coupled to the first segment about a second axis defined by the first segment that is oriented transverse to a longitudinal axis defined by the second segment, the second segment defining a second cavity configured to receive another portion of the elongate shaft including the bevel therein, the cap assembly having:
      a deployed configuration in which the first segment and the second segment are configured to form a contact barrier to cover the bevel,
      a first retracted configuration in which the second segment is moved with respect to the first segment and the base segment to expose the bevel and a first designated length of the elongate shaft to define a first maximum penetration depth of the of the needle system, the first maximum penetration depth defined between the bevel and a leading surface of the first segment, the leading surface of the first segment being a surface of the first segment positioned nearest the bevel, and
      a second retracted configuration in which the first segment and the second segment are moved with respect to the base segment to expose the bevel and a second designated length of the elongate shaft to define a second maximum penetration depth between the bevel and a leading surface of the base segment, the leading surface of the base segment being a surface of the base segment positioned nearest the bevel.

2. The cap assembly of claim 1, wherein the first segment pivots about the first axis relative to the base segment when moved between the retracted and deployed configurations.

3. The cap assembly of claim 1, further comprising an elongated slot formed axially through a sidewall of the first segment and the second segment, the elongated slot in physical communication with the first cavity and the second cavity, so that when the first segment or the second segment moves between the retracted and deployed configurations the tip portion passes through the elongated slot.

4. The cap assembly of claim 1, further comprising a clasp assembly comprising elements that are attached to the first segment and the base segment, so that when the first and base segments are in the deployed configuration, a clasp force is transferred across the elements and between the first segment and the base segment to selectively retain the first segment in the deployed configuration.

5. The cap assembly of claim 1, further comprising a hinge assembly pivotally coupling the base segment and the first segment such that the first segment is pivotable about the first axis relative the base segment between the deployed configuration and the second retracted configuration.

6. The cap assembly of claim 1, further comprising another hinge assembly pivotally coupling the second segment to the first segment such that the second segment is pivotable about the second axis with respect to the first segment and the base segment between the deployed configuration and first retracted configured.

7. The cap assembly of claim 6, wherein the first axis is parallel to the second axis, the first axis and the second axis positioned on opposite sides of the cap assembly.

8. A method of using a cap assembly for a needle system, the method comprising:
   mounting the cap assembly to a tip portion of the needle system with a base segment of the cap assembly received on a hub of the tip portion;
   retracting a first segment of the cap assembly to expose a designated distance of the tip portion such that the exposed distance of the tip portion defines a penetration depth of the needle system;
   deploying the first segment to form a contact barrier to cover a bevel of the tip portion; and
   selectively detaching a first portion of the first segment at a first set of perforations defined by the first segment or a second portion of the first segment at a second set of perforations defined by the first segment to increase the penetration depth of the needle system, the first set of perforations and the second set of perforations disposed circumferentially about the first segment perpendicular to and spaced apart along a longitudinal axis of the first segment, detachment of the first portion at the first set of perforations increasing the penetration depth a first amount and detachment of the second portion at the second set of perforations increasing the penetration depth a second amount greater than the first amount.

9. The method of claim 8, further comprising inserting the tip portion into a subject up to the designated distance when the tip portion is exposed.

10. The method of claim 8, wherein the step of retracting comprises pivoting the first segment of the cap assembly with respect to the base segment of the cap assembly.

11. The method of claim 8, wherein the step of retracting comprises moving the first segment of the cap assembly axially with respect to the base segment of the cap assembly.

12. The method of claim 8, wherein the tip portion comprises a shaft with the bevel on a free end thereof.

13. The method of claim 8, wherein the cap assembly is combined with the tip portion to form a kit.

14. A cap assembly for use with a needle system, the needle system having a hub and a tip portion, the tip portion including an elongate shaft extending away from the hub, the tip portion including a bevel on a free end of the elongate shaft opposite the hub, the cap assembly comprising:
   a base segment having a mouth configured to selectively secure the base segment to the needle system, the base segment defining a first cavity configured to receive the tip portion of the needle system therethrough and the mouth receive a portion of the hub therein; and
   a first segment defining a second cavity configured to receive the tip portion therein, the first segment moveably coupled to the base segment about an axis transverse to a longitudinal axis defined by the first segment, the first segment moveable between a deployed configuration in which the first segment is configured to enclose the bevel and a retracted configuration in which the first segment is configured to expose the bevel, the first segment defining:

a first set of perforations disposed circumferentially about the first segment perpendicular to the longitudinal axis of the first segment, a first portion of the first segment selectively detachable at the first set of perforations to define a first maximum penetration depth of the needle system, the first maximum penetration depth defined by a length of the elongate shaft exposed between the bevel and the first segment when the cap assembly is in the retracted configuration and is secured to the needle system, and a second set of perforations disposed circumferentially about the first segment perpendicular to the longitudinal axis of the first segment and spaced apart from the first set of perforations along the longitudinal axis of the first segment, a second portion of the first segment selectively detachable at the second set of perforations to define a second maximum penetration depth greater than the first maximum penetration depth, the second maximum penetration depth defined by a length of the elongate shaft exposed between the bevel and the first segment when the cap assembly is in the retracted configuration and is secured to the needle system.

15. The cap assembly of claim 14, wherein the first segment is coupled to the base segment such that the first cavity and the second cavity are substantially coaxial with one another, and wherein the first segment moves axially with respect to the base segment when moved between the retracted and deployed configurations.

16. The cap assembly of claim 15, wherein the first segment defines an aperture in physical communication with the second cavity at an end of the first segment positioned distally from the base segment, the bevel disposed through the aperture when the first segment is in the retracted configuration the, first and second maximum penetration depths defined between the bevel and the end of the first segment.

* * * * *